United States Patent
Matsunaga et al.

(10) Patent No.: US 12,097,497 B2
(45) Date of Patent: *Sep. 24, 2024

(54) CELL ACCOMMODATING CHIP

(71) Applicant: YAMATO SCIENTIFIC CO., LTD., Tokyo (JP)

(72) Inventors: Mariko Matsunaga, Tokyo (JP); Ken Tsukii, Tokyo (JP); Kenichi Kimura, Tokyo (JP); Toru Takahashi, Tokyo (JP); Jie Xu, Tokyo (JP); Takayuki Matsumoto, Tokyo (JP); Kohta Igarashi, Tokyo (JP)

(73) Assignee: YAMATO SCIENTIFIC CO., LTD., Tokyo (JP)

( * ) Notice: Subject to any disclaimer, the term of this patent is extended or adjusted under 35 U.S.C. 154(b) by 614 days.

This patent is subject to a terminal disclaimer.

(21) Appl. No.: 16/146,764

(22) Filed: Sep. 28, 2018

(65) Prior Publication Data

US 2019/0031993 A1 Jan. 31, 2019

Related U.S. Application Data

(63) Continuation of application No. PCT/JP2017/013561, filed on Mar. 31, 2017.

(30) Foreign Application Priority Data

Mar. 31, 2016 (JP) .................................. 2016-070969

(51) Int. Cl.
*C12M 3/00* (2006.01)
*B01L 3/00* (2006.01)
(Continued)

(52) U.S. Cl.
CPC ... *B01L 3/502753* (2013.01); *B01L 3/502715* (2013.01); *B01L 3/50855* (2013.01);
(Continued)

(58) Field of Classification Search
CPC ......... B01L 3/502753; B01L 3/502715; B01L 3/50855; B01L 2300/161; B01L 2300/168;
(Continued)

(56) References Cited

U.S. PATENT DOCUMENTS 4,495,289 A * 1/1985 Lyman et al. ......... C12M 23/38
422/504
8,323,973 B2 * 12/2012 Kanome ............... C12N 5/0068
435/405
(Continued)

FOREIGN PATENT DOCUMENTS

| CN | 1553188 A | 12/2004 |
|---|---|---|
| CN | 1771438 A | 5/2006 |

(Continued)

OTHER PUBLICATIONS

Extended European Search Report dated Oct. 14, 2019 for Application No. 17775525.3.
(Continued)

*Primary Examiner* — Nathan A Bowers
(74) *Attorney, Agent, or Firm* — Birch, Stewart, Kolasch & Birch, LLP

(57) ABSTRACT

A cell accommodating chip is adapted for use in a screening apparatus for searching for a predetermined cell based on optical information emitted from a substance on the cell accommodating chip and selectively collecting the cell searched for. The cell accommodating chip includes a substrate composed of a light-transmitting material, and a plurality of wells capable of accommodating cells, the plurality of wells being provided on at least one of main faces of the substrate. A surface of the cell accommodating chip having the plurality of wells is coated with a specific polymer having a crosslinked structure.

5 Claims, 11 Drawing Sheets

(51) Int. Cl.
*C12M 1/00* (2006.01)
*C12M 1/26* (2006.01)
*C12M 1/32* (2006.01)
*C12M 1/34* (2006.01)
*G01N 33/48* (2006.01)
*G01N 33/50* (2006.01)

(52) U.S. Cl.
CPC ............ *C12M 23/12* (2013.01); *C12M 23/20* (2013.01); *C12M 23/22* (2013.01); *C12M 33/04* (2013.01); *C12M 41/36* (2013.01); *G01N 33/48* (2013.01); *G01N 33/5005* (2013.01); *B01L 2300/161* (2013.01); *B01L 2300/168* (2013.01)

(58) Field of Classification Search
CPC ...... C12M 33/04; C12M 41/36; C12M 23/12; C12M 23/20; C12M 23/22; G01N 33/48; G01N 33/5005
See application file for complete search history.

(56) References Cited

U.S. PATENT DOCUMENTS

| | | | |
|---|---|---|---|
| 9,494,575 | B2 | 11/2016 | Jin et al. |
| 2003/0022216 | A1 | 1/2003 | Mao et al. |
| 2003/0219816 | A1 | 11/2003 | Solomon et al. |
| 2005/0014201 | A1 | 1/2005 | Deuthsch |
| 2006/0147949 | A1 | 7/2006 | Ha et al. |
| 2007/0105089 | A1 | 5/2007 | Deutsch |
| 2007/0148698 | A1 | 6/2007 | Solomon et al. |
| 2007/0148783 | A1 | 6/2007 | Solomon et al. |
| 2008/0175758 | A1* | 7/2008 | Matsumoto ............ C08J 7/0427 422/68.1 |
| 2009/0191626 | A1 | 7/2009 | Shogbon et al. |
| 2011/0189721 | A1 | 8/2011 | Deutsch |
| 2011/0212853 | A1 | 9/2011 | Cynis et al. |
| 2011/0294678 | A1 | 12/2011 | Jin et al. |
| 2012/0015824 | A1 | 1/2012 | Love et al. |
| 2012/0059111 | A1 | 3/2012 | Sandhu et al. |
| 2014/0011960 | A1 | 1/2014 | Konno et al. |
| 2014/0134729 | A1 | 5/2014 | Shogbon et al. |
| 2015/0017221 | A1 | 1/2015 | Hayashi et al. |
| 2016/0023209 | A1* | 1/2016 | Lenigk et al. .......... B01L 3/561 435/287.7 |
| 2016/0168294 | A1 | 6/2016 | Hayashi et al. |
| 2016/0333313 | A1 | 11/2016 | Shogbon et al. |
| 2016/0369123 | A1 | 12/2016 | Takada et al. |
| 2016/0370342 | A1 | 12/2016 | Kimura et al. |
| 2017/0023562 | A1 | 1/2017 | Jin et al. |
| 2018/0023053 | A1 | 1/2018 | Shogbon et al. |
| 2019/0048113 | A1 | 2/2019 | Hayashi et al. |
| 2019/0338246 | A1 | 11/2019 | Shogbon et al. |

FOREIGN PATENT DOCUMENTS

| | | | |
|---|---|---|---|
| CN | 1957093 | A | 5/2007 |
| CN | 101939362 | A | 1/2011 |
| CN | 103209717 | A | 7/2013 |
| CN | 103403140 | A | 11/2013 |
| CN | 104039949 | A | 9/2014 |
| EP | 2 184 345 | A1 | 5/2010 |
| JP | 2004-531390 | A | 10/2004 |
| JP | 2006-176720 | A | 7/2006 |
| JP | 2006-299045 | A | 11/2006 |
| JP | 4148367 | B1 | 9/2008 |
| JP | 2012-52843 | A | 3/2012 |
| JP | 2012-93290 | A | 5/2012 |
| JP | 2012-511155 | A | 5/2012 |
| JP | 2013-519891 | A | 5/2013 |
| JP | 2013-247926 | A | 12/2013 |
| JP | 5614179 | B2 | 10/2014 |
| WO | WO 03/035824 | A1 | 5/2003 |
| WO | WO 2015/133337 | A1 | 9/2015 |
| WO | WO 2015/151881 | A1 | 10/2015 |

OTHER PUBLICATIONS

International Search Report (PCT/ISA/210) issued in PCT/JP2017/013561, dated Jun. 20, 2017.
Written Opinion of the International Searching Authority (PCT/ISA/237) issued in PCT/JP2017/013561, dated Jun. 20, 2017.
International Preliminary Report on Patentability and English translation of the Written Opinion of the International Searching Authority (forms PCT/IB/373 and PCT/ISA/237), dated Oct. 2, 2018, for corresponding International Application No. PCT/JP2017/013561.
Extended European Search Report dated Jan. 3, 2020 for corresponding European Patent Application No. 17775524.6.
Chinese Office Action and Search Report for Chinese Application No. 201780021248.8, dated May 14, 2021, with English translation of the Office Action.
Chinese Office Action and Search Report for Chinese Application No. 201780021391.7, dated May 27, 2021 with English translation of the Office Action.
Japanese Office Action, dated Jan. 18, 2021, for Japanese Application No. 2018-509650, with an English translation.
Japanese Office Action, dated Nov. 18, 2020, for Japanese Application No. 2018-509649, with an English translation.
Decision of Refusal issued in Japan Application No. 2018-509649, dated Aug. 3, 2021.
Office Action dated Mar. 26, 2021 in the relevant U.S. Appl. No. 16/146,792.
Chinese Office Action for Chinese Application No. 201780021391.7, dated Nov. 8, 2021, with English translation.
Chinese Office Action and Search Report for corresponding Chinese Application No. 201780021248.8. dated Nov. 26, 2021, with English translation.
Li et al., "Concise Dictionary of Natural Sciences," Shandong University Press, Sep. 1988 (70 pages total), with partial English translation.
Lui et al., "Introduction to Molecular Ecology," Harbin Institute of Technology Press, Mar. 2012 pp. 278-290 (23 pages total), with partial English translation.
International Preliminary Report on Patentability, dated Oct. 2, 2018, and the English translation of the Written Opinion of the International Searching Authority, dated Jul. 4, 2017, for International Application No. PCT/JP2017/013560.
International Search Report for International Application No. PCT/JP2017/013560, dated Jul. 4, 2017, with English translation.
Written Opinion of the International Searching Authority for International Application No. PCT/JP2017/013560, dated Jul. 4, 2017.
U.S. Office Action for U.S. Appl. No. 16/146,792, dated Oct. 28, 2021.
Chinese Office Action for Chinese Application No. 201780021248.8, dated May 7, 2022, with English translation.
U.S. Office Action for U.S. Appl. No. 16/146,792, dated Jun. 22, 2022.
Chinese Rejection Decision for Chinese Application No. 201780021391.7, dated Apr. 22, 2022, with an English translation.
U.S. Appl. No. 16/146,792, filed Sep. 28, 2018.

* cited by examiner

CELL ACCOMMODATING CHIP

CROSS REFERENCE TO RELATED APPLICATIONS

This is a continuation application of International Patent Application No. PCT/JP2017/013561 filed Mar. 31, 2017, which claims the benefit of Japanese Patent Application No. 2016-070969, filed Mar. 31, 2016, the full contents of both of which are hereby incorporated by reference in their entirety.

BACKGROUND

Technical Field

The present disclosure relates to a cell accommodating chip capable of accommodating a plurality of cells in screening for a target sample, and particularly relates to a cell accommodating chip for detecting a cell to be a target sample by irradiating wells and cells with light and based on fluorescence emitted by a substance bound onto the cell accommodating chip, and selectively sucking and collecting the cell.

Background

In the related art, screening apparatuses have been widely used as apparatuses for identifying and isolating minute analytes, such as cells, in research, inspection, and so on in the medical field. In recent years, in the research and inspection institutions, there are demands for achieving identification and isolation without destroying analytes and for increasing the efficiency of research and inspection by more exactly performing these treatments. In particular, in a predetermined field, since there is a growing demand for identifying and isolating, on a single cell basis, a specific cell from a large number of cells, improvement of accuracy and enhancement of efficiency are required also in such identification and isolation treatments on a single cell basis.

In identification and isolation treatments of cells performed with a nondestructive manner, it is desirable to retain a medium containing a large number of fine particles on a cell accommodating chip such that a target sample and a nontarget sample are clearly distinguished from each other. Accordingly, in the related art, for example, a method for identifying a target sample using a microwell array chip including a coating layer prepared by binding an anti-immunoglobulin (Ig) antibody to a part of an upper surface of the chip, dispensing an antibody-secreting cell to each well of the microwell array chip to bind an antibody secreted from at least some of the cells accommodated in the well to the anti-Ig antibody of the coating layer, and detecting the secreted antibody with a fluorescence-labeled antigen is disclosed (Japanese Patent No. 4148367).

In addition, in order to selectively bind a desired target sample from an external environment or collectively remove nontarget samples from a surface, a functional coating prepared by supplying, to a plate-like support, a low nonspecific binding matrix immobilized on the support and an active component covalently bonded in the nonspecific binding matrix by physically entangling is disclosed (National Publication of International Patent Application No. 2004-531390).

However, with the technique of Japanese Patent No. 4148367, since the chip upper surface must be kept wet during the period from binding of an anti-Ig antibody to a part of the chip upper surface until identification of the target sample, the anti-Ig antibody cannot be sustained for a long time. In addition, since a cell may adhere to an inner surface of a well during antibody secretion by the cell, it is difficult to collect the cell, and even if the cell was collected, it is very likely to damage the cell that is a target sample.

In addition, National Publication of International Patent Application No. 2004-531390 discloses a structure in which a target sample is selectively bound to a functional coating disposed on an upper surface of a plate-like support, but not a structure retaining a single cell in each well, and it cannot be said that accuracy and efficiency of identification and isolation of a specific cell on a cell basis are high.

The present disclosure is related to providing a cell accommodating chip that can identify and isolate a target sample with high accuracy and high efficiency, is simple to handle, and can easily collect a cell without damaging the cell.

SUMMARY

According to a first aspect of the present disclosure, a cell accommodating chip capable of accommodating a plurality of cells is a cell accommodating chip adapted for use in a screening apparatus for searching for a predetermined cell based on optical information emitted from a substance on the cell accommodating chip and selectively collecting the cell searched for. The cell accommodating chip includes a substrate composed of a light-transmitting material and a plurality of wells capable of accommodating cells on at least one of main faces of the substrate, wherein a surface of the cell accommodating chip having the plurality of wells is coated with a polymer having a crosslinked structure and including a structural unit derived from a monomer represented by the following General Formula [1], a structural unit derived from a monomer represented by the following General Formula [2], and a structural unit derived from a monomer represented by the following General Formula [3].

Formula [1]

General Formula [1]

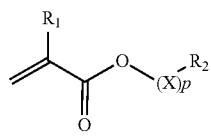

wherein $R_1$ represents a hydrogen atom or a methyl group; $R_2$ represents a hydrogen atom or an alkyl group having 1 to 20 carbon atoms; X represents an alkylene glycol residue having 1 to 10 carbon atoms; and p represents an integer of 1 to 100, and when p is an integer of greater than or equal to 2 but less than or equal to 100, a plurality of X may be the same or different, Formula [2]

General Formula [2]

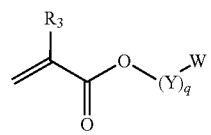

wherein $R_3$ represents a hydrogen atom or a methyl group; Y represents an alkyl group or an alkylene glycol residue having 1 to 10 carbon atoms; W represents an active ester group; and q represents an integer of 1 to 20, and when q is an integer of greater than or equal to 2 but less than or equal to 20, a plurality of Y may be the same or different, Formula [3]

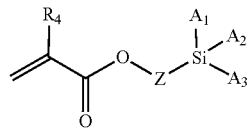

General Formula [3]

wherein $R_4$ represents a hydrogen atom or a methyl group; Z represents an alkyl group having 1 to 20 carbon atoms; and at least one of $A_1$, $A_2$, and $A_3$ is a hydrolyzable alkoxy group, and the others represent alkyl groups.

According to the present disclosure, a surface of a cell accommodating chip having a plurality of wells is coated with a specific polymer. Consequently, the chip surface has a low cell adhesion property, and also has affinity to a specific binding material having affinity to a produced substance that is produced by a cell accommodated in any of the wells. Since a chip of the related art has a structure in which a substance having affinity to a produced substance is bound on the chip in advance, it is difficult to preserve the chip for a long period of time, and accuracy may decrease due to drying or the like. In contrast, according to the present disclosure, since the surface of the cell accommodating chip has affinity to the specific binding material, it is not necessary to bind a specific binding material having affinity to the produced substance on the cell accommodating chip in advance, and a reduction in accuracy due to drying or the like can be prevented.

In addition, due to the affinity of the surface of the cell accommodating chip to the specific binding material, the specific binding material binds to the surface of the cell accommodating chip having wells and the produced substance produced by the cell in the well binds to the specific binding material. Accordingly, the well itself can be used as a labeling site in identification of a target sample, and the target sample can be identified without damaging the cell. Furthermore, since the surface of the cell accommodating chip has a low cell adhesion property, the cell in the well can be prevented from adhering to the surface of the cell accommodating chip, the cell that is a target sample can be collected at high efficiency without requiring coating treatment using a blocking reagent or the like, and in cell collection, the cell can be collected without being damaged.

BRIEF DESCRIPTION OF DRAWINGS

The above-described objects and other objects, features, and advantages will become more apparent from the preferred embodiments described below and the accompanying drawings below.

DETAILED DESCRIPTION

Figure 1:
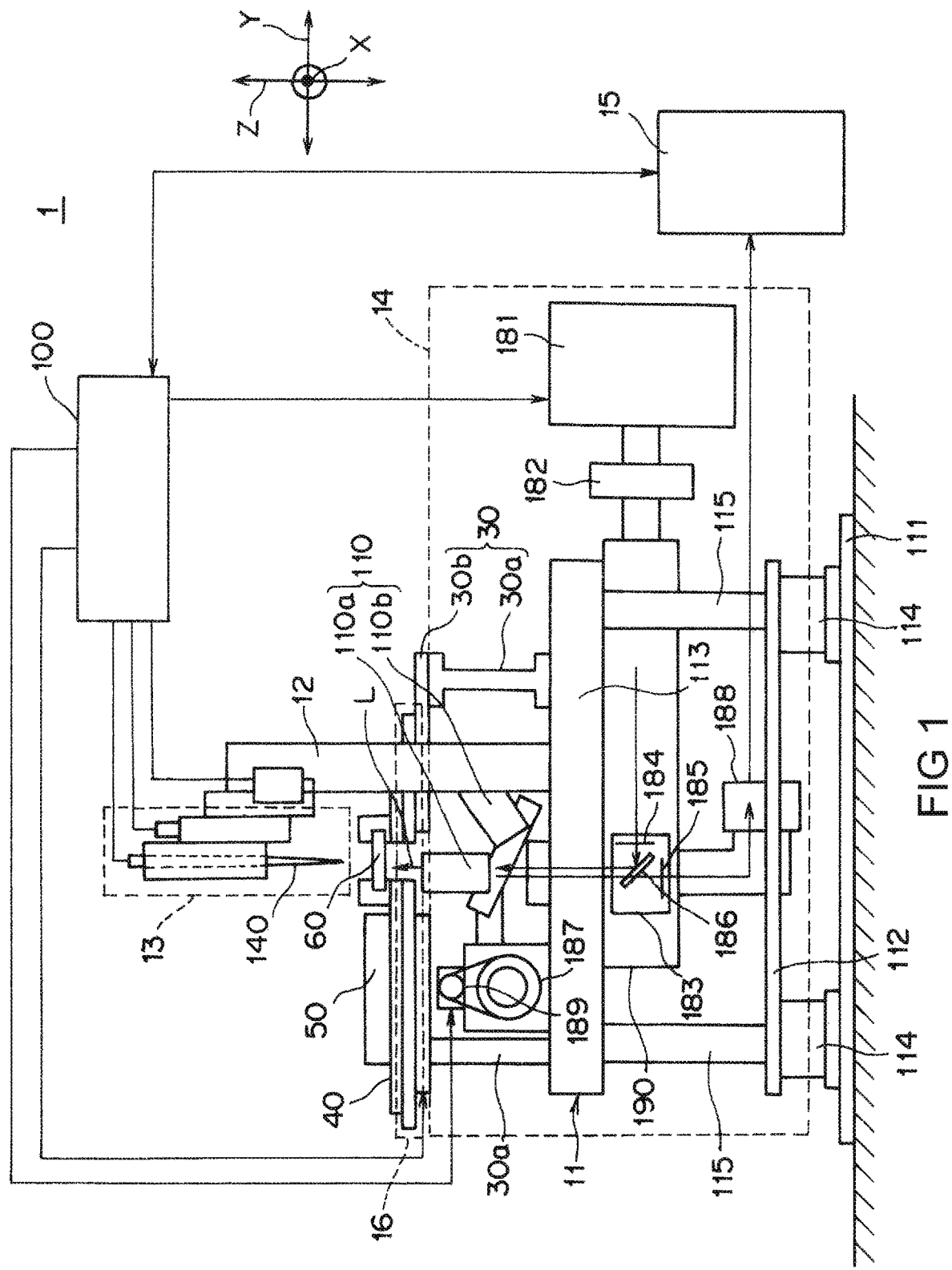
FIG. 1 is a side view schematically illustrating a structure of a screening apparatus using a cell accommodating chip according to an embodiment of the present disclosure.

Embodiments of the present disclosure will now be described in detail referring to the drawings.

Structure of Screening Apparatus

Figure 2:
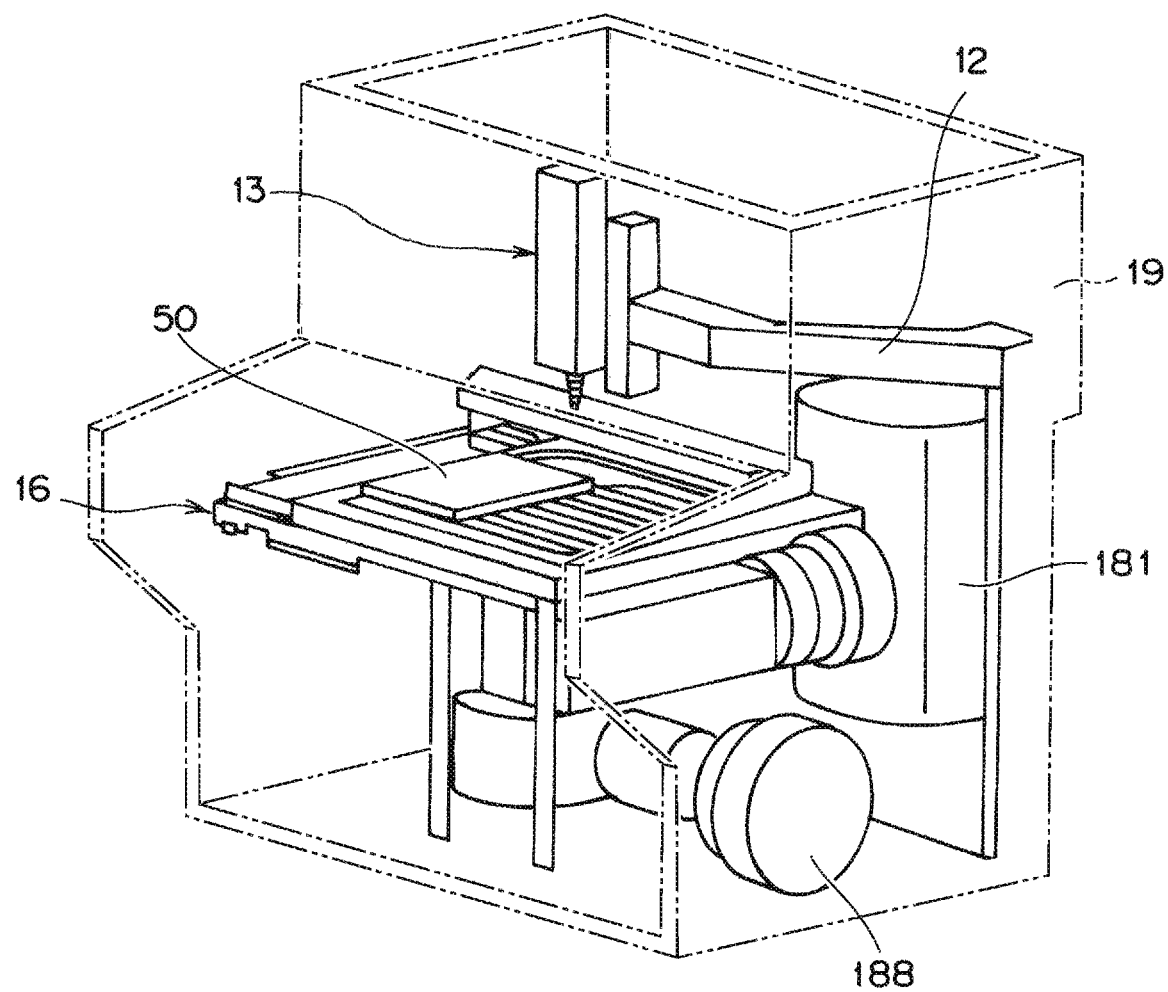
FIG. 2 is a perspective view of the screening apparatus of FIG. 1.

FIG. 1 is a side view schematically illustrating a structure of a screening apparatus using a cell accommodating chip according to the present embodiment, and FIG. 2 is a perspective view of the screening apparatus shown in FIG. 1. The screening apparatus shown in FIGS. 1 and 2 is merely an example, and the embodiment of the screening apparatus is not limited to that shown in FIGS. 1 and 2. For convenience of explanation, the direction perpendicular to the plane of paper of FIG. 1 is defined as the X-direction, the horizontal direction is defined as the Y-direction, and the direction perpendicular to the X-direction and the Y-direction is defined as the Z-direction.

In FIGS. 1 and 2, the screening apparatus, 1 is an apparatus that searches for a predetermined cell as a target sample based on optical information emitted from a plurality of microparticles (e.g., cells of living) in a cell accommodating chip 60, and selectively sucks and picks up a cell in a well that accommodates a cell satisfying a collecting condition to collect the cell in an accommodating plate 50.

Specifically, the screening apparatus 1 includes a base 11, a supporting section 12 (see FIG. 2), a collecting section 13, a measuring section 14, an image analyzing section 15, and a moving section 16, and, as shown in FIG. 2, all the sections are covered with a cover 19 for preventing penetration of light and foreign substances from outside.

The base 11 is a main body frame for holding each element of the screening apparatus 1. This base 11 includes plate members 111, 112, and 113 disposed substantially horizontally and holds the collecting section 13, the measuring section 14, and the moving section 16 via these plate members. The plate members 111 and 112 are fixed parallel to each other by a plurality of vertical members 114, and the plate members 112 and 113 are fixed parallel to each other by a plurality of vertical members 115. The vertical members 114 are made of a material shielding a vibration and are configured to be adjustable in height.

The supporting section 12 and a supporting table 30 are fixed on the plate member 113 located at the uppermost position of the plurality of plate members. The supporting section 12 is arranged on the plate member 113 extending vertically along the Z-direction. The supporting table 30 includes a leg section 30a and a support plate 30b. The plate members 111, 112, and 113 and the support plate 30b are arranged with a predetermined interval therebetween in the Z-direction.

The moving section 16 is mounted and fixed on the support plate 30b of the supporting table 30. A mounting, table 40, an accommodating plate 50, and a cell accommodating chip 60 are mounted on the moving section 16. The moving section 16 can move and position the mounting table 40, i.e., the accommodating plate 50 and the cell accommodating chip 60 mounted on the mounting table 40, along the X-direction and/or the Y-direction.

Figure 3:
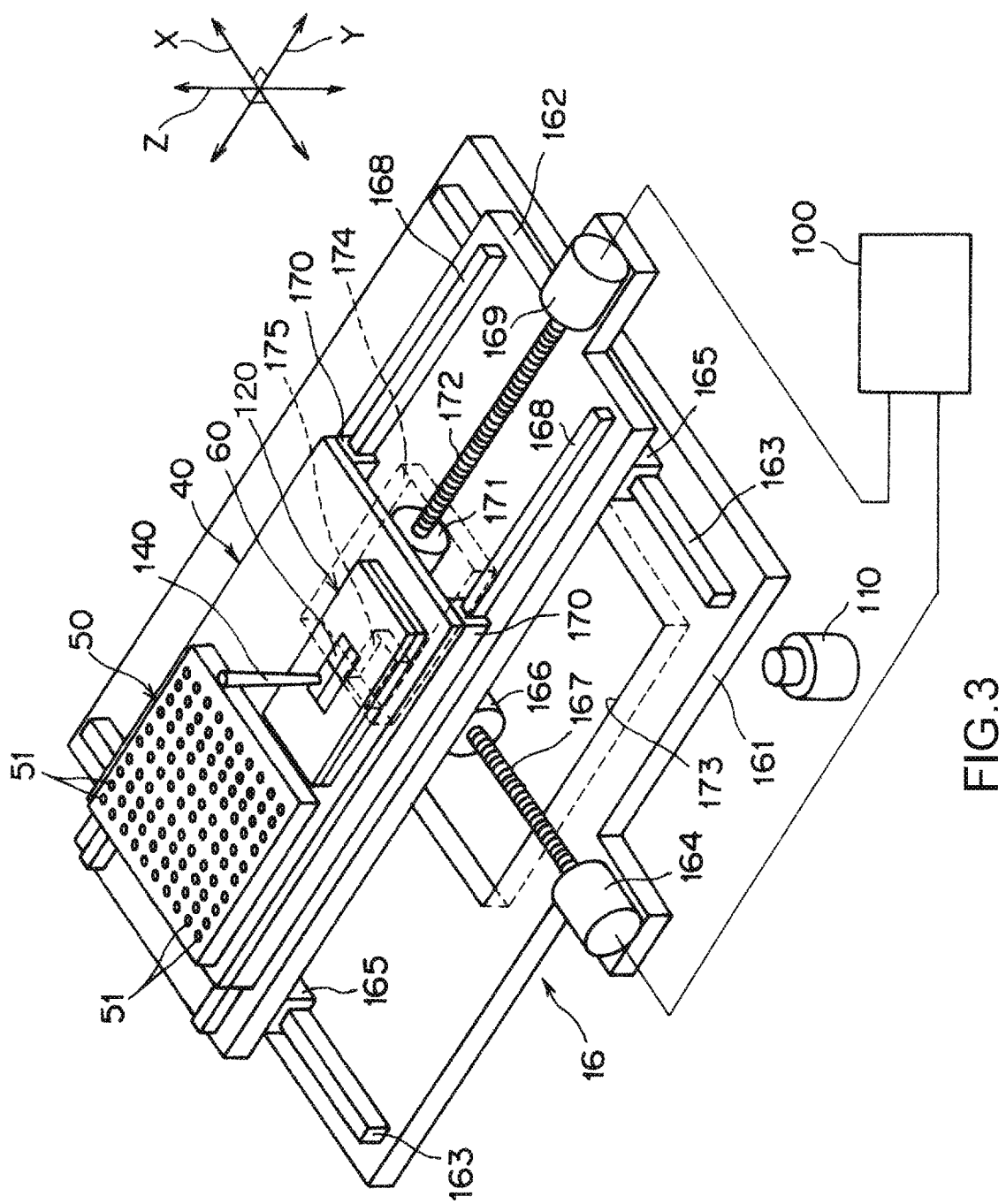
FIG. 3 is a perspective view illustrating details of a moving section and a mounting table shown in FIG. 2.

FIG. 3 is a perspective view illustrating details of the moving section 16 and the mounting table 40 shown in FIG. 2.

As shown in FIG. 3, the moving section 16 includes a table 161, and a table 162 arranged on said table. The table 161 is secured to the supporting table 30 and mounted so as to be capable of moving and positioning the table 162 along the X-direction. The table 162 is mounted so as to be capable of moving and positioning the mounting table 40 along the Y-direction.

Guide rails 163, 163 and a motor 164 are disposed on the upper surface of the table 161. Engaging members 165, 165 having a U-shaped cross section and a nut 166 are disposed on the lower surface of the table 162. The engaging members 165, 165 are movably engaged with the guide rails 163, 163, respectively. A feed screw 167 of the motor 164 is screwed to the nut 166.

The motor 164 is electrically connected to a control unit 100 and is operated in response to a command from the control unit 100 to rotate the feed screw 167. Consequently, the table 162 is moved and positioned along the X-direction.

Guide rails 168, 168 and a motor 169 are disposed on the upper surface of the table 162. Engaging members 170, 170 having a U-shaped cross section and a nut 171 are disposed on the lower surface of the mounting table 40. The engaging members 170, 170 are movably engaged with the guide rails 168, 168, respectively. A feed screw 172 of the motor 169 is screwed to the nut 171.

The motor 164 is electrically connected to the control unit 100 and is operated in response to a command from the control unit 100 to rotate the feed screw 172. Consequently, the mounting table 40 is moved and positioned in the Y-direction.

The table 161 has an opening 173, the table 162 has an opening 174, and the mounting table 40 has an opening 175. These openings 173, 174, and 175 have respective sizes such that the openings always overlap each other even if the table 162 moves in the X-direction and the mounting table 40 moves in the Y-direction. Through these openings 173, 174, and 175, the cells on the cell accommodating chip 60 on the mounting table 40 are irradiated with light L from the objective lens 110 side of the measuring section 14.

In addition, even if the table 162 moves in the X-direction and the mounting table 40 moves in the Y-direction, the light L from the objective lens 110 side passes through the openings 173, 174, and 175 and irradiates the cells on the cell accommodating chip 60 on the mounting table 40. That is, it is possible to generate fluorescence from a cell and/or a well accommodating a cell at any relative position of the tables 161 and 162 and the mounting table 40.

Figure 4:
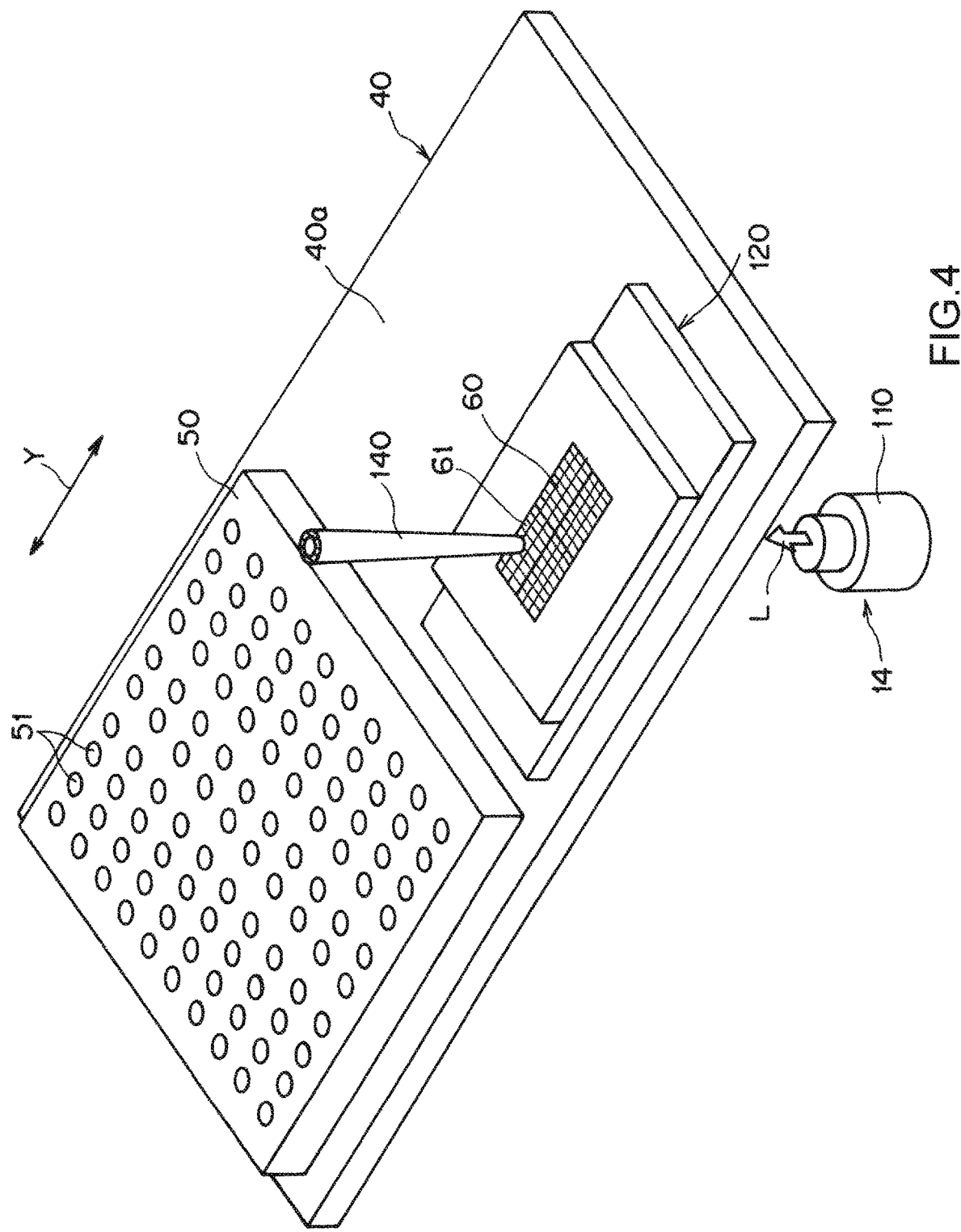
FIG. 4 is a perspective view illustrating a structure of the mounting table shown in FIG. 3.

FIG. 4 is a perspective view illustrating structures of the accommodating plate 50 and the cell accommodating chip 60 on the mounting table 40 shown in FIG. 3.

The mounting table 40 is, for example, a rectangular plate-like member, and the accommodating plate 50 and the cell accommodating chip 60 are detachably mounted on a mounting surface 40a of the mounting table 40 sequentially in the Y-direction.

The accommodating plate 50 is a plate-like member and is provided with a large number of wells 51 arranged at constant intervals along the X-direction and the Y-direction in a matrix form. These wells 51 form a collecting-and-storing section that can separately collect and store cells as target samples when the cells are sequentially ejected from a suction/discharge capillary 140. The wells 51 of the accommodating plate 50 are, for example, recessed portions having a substantially U-shaped vertical-direction cross section or a recessed portions having a cup shape.

The cell accommodating chip 60 is secured on the mounting surface 40a of the mounting table 40 by a securing member 120, and the securing member 120 is positioned at and fixed to a predetermined position of the mounting table 40.

Figure 5:
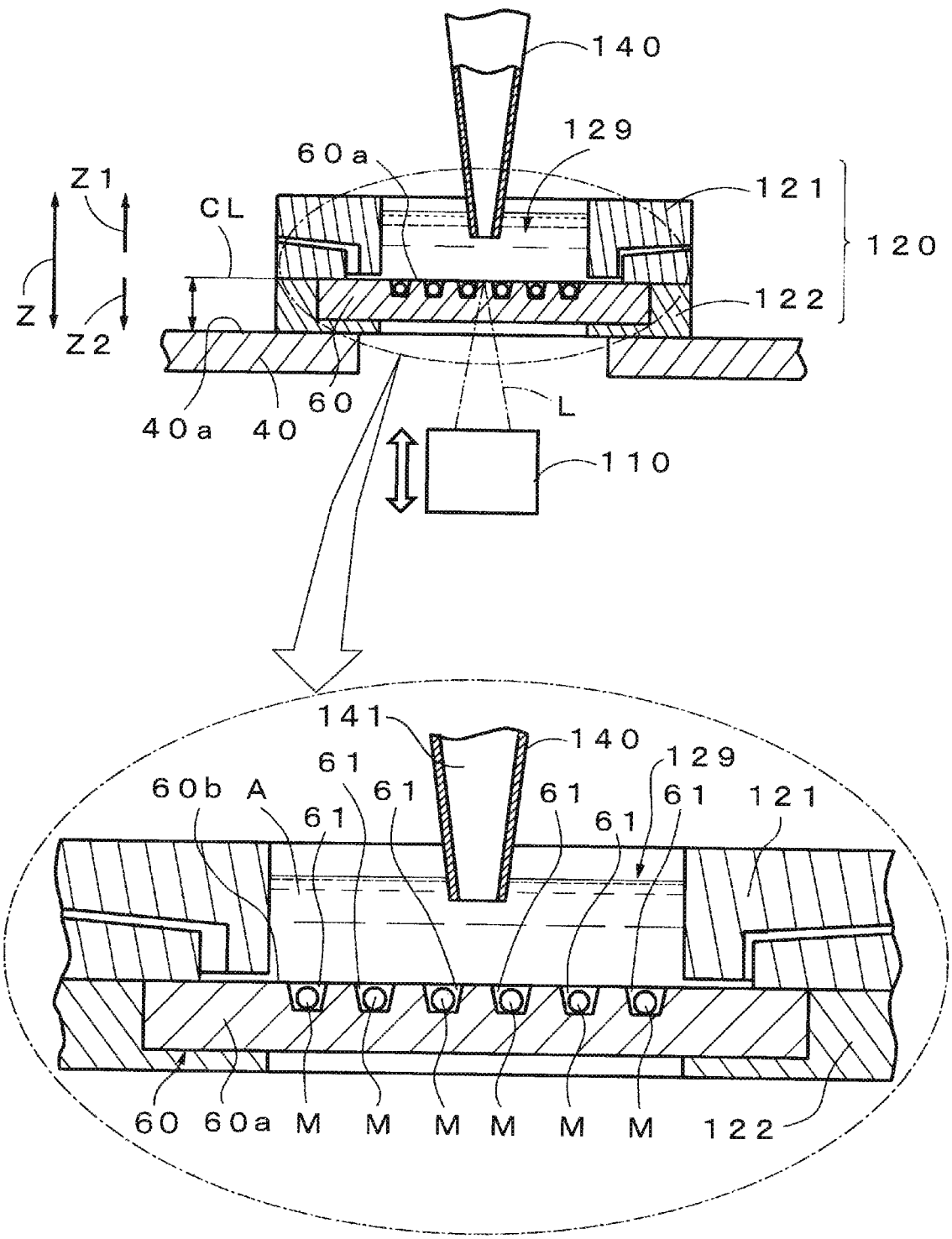
FIG. 5 is an enlarged cross-sectional view illustrating the structures of a cell accommodating chip and a securing member of the cell accommodating chip.

FIG. 5 is an enlarged cross-sectional view illustrating the structures of the cell accommodating chip 60 and the securing member 120. As shown in the drawing, the securing member 120 is structured such that the cell accommodating chip 60 can be secured and held at a position of a reference plane CL at a certain height with respect to the mounting surface 40a of the mounting table 40. Specifically, the securing member 120 includes frames 121 and 122 arranged so as to surround the edge of the cell accommodating chip 60 and holds the cell accommodating chip 60 in cooperation with these members.

The cell accommodating chip 60 is arranged between the frames 121 and 122 in the Z-direction and is sandwiched between the frames 121 and 122 so as to be in pressure contact with each of the frames 121 and 122. Consequently, the sealing property between the cell accommodating chip 60 and the frame 121 is ensured.

In the state in which the cell accommodating chip 60 is being in pressure contact with the frame 121, the upper surface 60b of the cell accommodating chip 60 is positioned at the reference plane CL via the frame 122. Consequently, it is possible to precisely control the distances in the Z-direction from the upper surface 60b of the cell accommodating chip 60 to the objective lens 110 of the measuring section 14 and to the accommodating plate 50. In other words, it possible to precisely control the position of a cell M in a well 61 of the cell accommodating chip 60 and the distance between the objective lens 110 of the measuring section 14 and the accommodating plate 50.

The frame 121 includes a liquid-holding section 129 disposed at the central part in the plane direction of the frame and above the cell accommodating chip 60 and holding a liquid A and is thereby structured so as to be capable of holding each type of liquid, such as a medium, a reagent solution, and a reaction solution. That is, the liquid-holding section 129 is formed in an internal space of the frame 121. The frame 121, is openable with respect to the frame 122 by using, for example, a hinge mechanism section (not shown in the drawing), which allows the cell accommodating chip 60 in the securing member 120 to be taken out and be replaced with a new cell accommodating chip. The cell accommodating chip 60 is a plate-like member capable of accommodating a plurality of cells M. Detailed structure of the cell accommodating chip 60 will be described below.

The collecting section 13 includes a suction/discharge capillary 140 for isolating the identified cell M as a target sample. The suction/discharge capillary 140 is a tapered hollow member whose diameter decreases along the Z2-direction (downward direction) and has a conduit 141 formed in the inside.

Returning to FIG. 1, the measuring section. 14 irradiates a region including a plurality of wells 61 of the cell accommodating chip 60 with light L to generate fluorescence from a cell M and/or a well 61 accommodating a cell or in the vicinity thereof in the region, and receives the fluorescence. The fluorescence from the cell M and/or the well 61 accommodating a cell or in the vicinity thereof that received the light is subjected to image analysis by the image analyzing section 15.

Specifically, the measuring section 14 irradiates the cell accommodating chip 60 and cells M accommodated in the cell accommodating chip 60 with light guided from at least one light source and hence acquires shape and position information from transmitted light, reflected light, or fluorescence and brightness information, such as fluorescence and chemiluminescence, with a resolution finer than the average size of microparticles and also acquires information on, for example, the shape of the cell accommodating chip 60 itself and the positional coordinate and size of the wells 61 arranged on the cell accommodating chip 60.

The measuring section 14 includes an objective lens 110, and the objective lens 110 guides light to the cell accommodating chip 60. The objective lens 110 is arranged below the cell accommodating chip 60 and the moving section 16, and the suction/discharge capillary 140 is arranged above the cell accommodating chip 60 and the moving section 16. That is, the cell accommodating chip 60 and the moving section 16 are arranged between the objective lens 110 and the suction/discharge capillary 140 in the Z-direction.

The measuring section 14 includes an excitation light source 181 as a light source, an optical filter (excitation filter) 184 for selecting only a desired excitation wavelength band from light irradiated from the excitation light source 181, an optical filter (fluorescence filter) 185 for selecting only a desired wavelength band of optical information from the cell accommodating chip 60, a fluorescence filter unit 183 includes a dichroic mirror 186 for switching the optical path depending on the difference between the wavelength bands of the excitation light and the optical information, an objective lens 110 for guiding the light emitted from the excitation light source 181 to the cell accommodating chip 60 and collecting optical information obtained from the cell accommodating chip 60, a focus unit 187 having an automatic focus function capable of moving the objective lens 110 in the optical axis direction, and a light-receiving section 188 as a light-detecting section for detecting optical information from a measurement target. The fluorescence filter unit 183 and the light-receiving section 188 are fixed to an epifluorescence unit 190.

The excitation light source 181 includes, for example, a laser light source or a mercury lamp. A shutter unit 182 is arranged between the excitation light source 181 and the fluorescence filter unit 183 and it is possible that the shutter unit 182 blocks light L produced by the excitation light source 181 before reaching the fluorescence filter unit 183 when the shutter unit 182 does not irradiate the cell M on the cell accommodating chip 60 with light L.

Furthermore, the measuring section 14 includes a half mirror (not shown in the drawing), and by switching the half mirror and the fluorescence filter unit 183, irradiates an observation target with a part of the light from the excitation light source 181, and, at the same time, a part of the reflection light from the observation target is guided to the light-receiving section 188, which allows measurement of the shape and position information of the upper surface 60b of the cell accommodating chip 60 and the wells 61 formed on the upper surface.

In the measuring section 14, a plurality of objective lens 110a, 110b, . . . are rotated, for example, in a revolve manner, and thereby an objective lens of a required magnification can be positioned below the cell accommodating chip 60. The focus unit 187 can perform focus adjustment of the objective lens 110 on a microparticle M on the cell accommodating chip 60 by, for example, operating the motor 189 in response to a command from the control unit 100 and moving and positioning, for example, the objective lens 110, disposed below the cell accommodating chip 60, along the Z-direction.

The image analyzing section 15 calculates the fluorescent brightness of at least a cell M and/or a well 61 accommodating a cell or in the vicinity thereof emitting fluorescence of a maximum intensity among a plurality of cells M in the respective wells 61 and/or the wells 61 accommodating cells or in the vicinities thereof.

Specifically, the image analyzing section 15 acquires at least data for verifying the presence of a cell M satisfying a brightness condition, which can be set by an observer, in each well 61 by analyzing the measured shape information and optical information. The image analyzing section 15 extracts optical information from a cell M and/or a well 61 accommodating a cell or in the vicinity thereof by matching the positional coordinate information of the well 61 by transmitted light or reflected light and the optical information of fluorescence/chemiluminescence. The measuring section 14 has an automatic focus function and is capable of performing measurement while being focused at a predetermined position and capable of determining a positional relationship between the distal end of the suction/discharge capillary 140 and the upper surface of the cell accommodating chip 60 by automatically focusing both of them.

The control unit 100 detects, in an X-Y plane, the position of a well 61 emitting fluorescence having a brightness satisfying a collecting condition. The control unit 100 is capable of positioning a well 61 of the cell accommodating chip 60 on the moving section 16 directly below the suction/discharge capillary 140 by sending, a control driving signal to the motors 164 and 169 shown in FIG. 3. That is, the suction/discharge capillary 140 is configured so as to be capable of targeting a specific cell to suck the cell in the well. In addition, the suction/discharge capillary 140 is capable of sucking a single or a plurality of cells from a well selected from a plurality of wells, i.e., a well accommodating a cell satisfying a predetermined collecting condition. Furthermore, the suction/discharge capillary 140 is capable of discharging the sucked single or plurality of cells into a predetermined well 51 of the accommodating plate 50.

Structure of Cell Accommodating Chip

Figure 6:
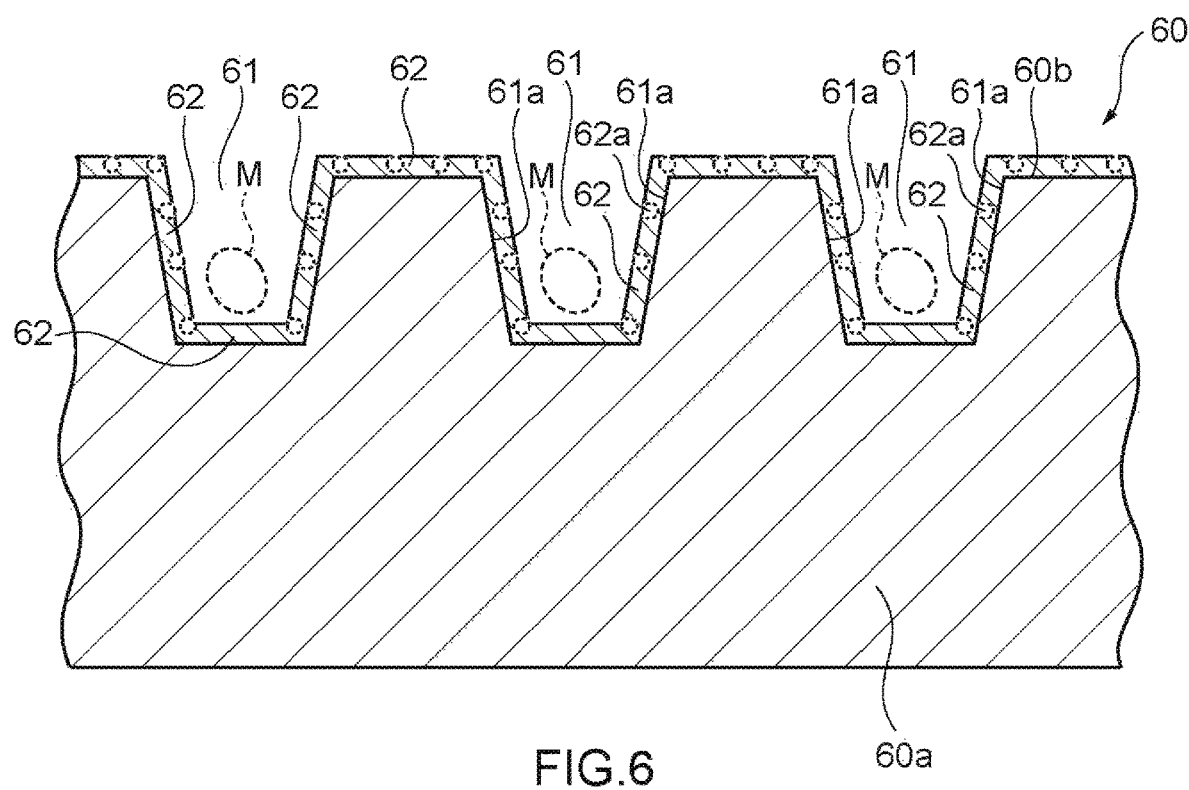
FIG. 6 is a partial cross-sectional view illustrating the detailed structure of the cell accommodating chip shown in FIG. 5.

FIG. 6 is a partial cross-sectional view illustrating the detailed structure of the cell accommodating chip 60 shown in FIG. 5. As shown in the drawing, the cell accommodating chip 60 includes a substrate 60a composed of a light-transmitting material and a plurality of wells 61, 61, . . . , disposed on the upper surface 60b (at least one of main surfaces) of the substrate and capable of accommodating a plurality of cells M on one-to-one basis.

The cell accommodating chip 60 includes a coating layer 62 formed on the inner surface 61a of each well constituting the plurality of wells 61, 61, . . . , and on the upper surface 60b of the substrate 60a (surface of the cell accommodating chip). The coating layer 62 may be formed on only the inner surface 61a of the well 61 or may be formed on both the inner surface 61a of the well 61 and the upper surface 60b of the substrate 60a. That is, although the coating layer 62 shown in FIG. 6 is drawn so as to thoroughly coat the inner surface 61a and the upper surface 60b, the coating layer 62 need not necessarily coat the entire inner surface 61a and upper surface 60b, as long as the effects of the present disclosure are achieved.

The cell accommodating chip 60 is composed of, for example, glass, plastic, or a material containing any of them as a main component, and a large number of wells 61 are arranged in, for example, a matrix form on the upper surface 60b. Each well 61 is a recessed portion having a vertical cross section of a substantially trapezoidal shape or a recessed portion having a substantially cup shape, and a horizontal cross-sectional shape of the well 61 is preferably substantially circular. The well 61 has a size corresponding to the accommodation of a single cell M when cells M are dispensed or collectively injected on the cell accommodating chip 60. For example, when the horizontal cross-sectional shape of the well 61 is a circle, the inner diameter and the depth of the well are each preferably slightly greater than the diameter of a cell, e.g., about 20 μm, for a cell M having a diameter of 15 μm. It is preferable that the well 61 has a size corresponding to a single cell M and is more preferable that it has a size allowing only a single cell M to enter.

The coating layer 62 includes a polymer having a cross-linked structure and including a structural unit derived from a monomer represented by General Formula [1] described above, a structural unit derived from a monomer represented by General Formula [2] described above, and a structural unit derived from a monomer represented by General Formula [3] described above (hereinafter, this polymer is also simply referred to as "polymer"). Here, the crosslinked structure is typically formed by involvement of the structural unit derived from a monomer represented by General Formula [3]. This will be described in more detail below.

In General Formula [1] described above, the "alkylene glycol residue" means an "alkyleneoxy group" (—R—O—, where R is an alkylene group) remaining after a condensation reaction of the hydroxyl group at one end or both ends of alkylene glycol (HO—R—OH, where R is an alkylene group) with another compound. For example, the "alkylene glycol residue" of methylene glycol (HO—CH$_2$—OH) is a methyleneoxy group (—CH$_2$—O—), and the "alkylene glycol residue" of ethylene glycol (HO—CH$_2$—CH$_2$—OH) is an ethyleneoxy group (—CH$_2$—CH$_2$—O—).

In General Formula [1], $R_1$ is a hydrogen atom or a methyl group, and $R_2$ is a hydrogen atom or an alkyl group having 1 to 20 carbon atoms. The number of carbon atoms of the alkylene glycol residue X is 1 to 10, more preferably 1 to 6, further preferably 2 to 4, more further preferably 2 or 3, and most preferably 2. The repeating number p of the alkylene glycol residues is an integer of 1 to 100, preferably an integer of 2 to 100, more preferably an integer of 3 to 100, further preferably an integer of 2 to 95, and most preferably an integer of 20 to 90. When the repeating number p is greater than equal to 2 but less than or equal to 100, the numbers of carbon atoms of the alkylene, glycol residues X repeated in the chain may be the same or different.

Examples of the monomer represented by General Formula [1] include methoxy polyethylene glycol (meth)acrylate; (meth)acrylates of a hydroxyl group-monosubstituted ester, such as 2-hydroxyethyl (meth)acrylate, 2-hydroxypropyl (meth)acrylate, and 2-hydroxybutyl (meth)acrylate; glycerol mono(meth)acrylate; (meth)acrylate having polypropylene glycol as a side chain; 2-methoxyethyl (meth)acrylate; 2-ethoxyethyl (meth)acrylate; methoxy diethylene glycol (meth)acrylate; ethoxy diethylene glycol (meth)acrylate; and ethoxy polyethylene glycol (meth)acrylate. Considering the availability, methoxy polyethylene glycol methacrylate is preferable. The term "(meth)acrylate" refers to methacrylate or acrylate. These monomers may be used alone or in combination of two or more thereof.

In the polymer, the proportion of the structural unit derived from a monomer represented by General Formula [1] is usually 30 to 98 mol %, preferably 50 to 97 mol %, and more preferably 60 to 97 mol % based on the total structural units of the polymer.

In General Formula [2] described above, $R_3$ is a hydrogen atom or a methyl group, and the number of carbon atoms of the alkylene glycol residue Y is 1 to 10, more preferably 1 to 6, further preferably 2 to 4, more further preferably 2 or 3, and most preferably 2. The repeating number q of the alkylene glycol residues Y is an integer of 1 to 20, more preferably an integer of 2 to 18, further preferably an integer of 3 to 16, and most preferably an integer of 4 to 14. When the repeating number q is greater than or equal to 2 but less than or equal to 20, the numbers of carbon atoms of the alkylene glycol residues repeated in the chain may be the same or different.

The "active ester group" refers to a group of esters activated for a nucleophilic reaction by including an electron-withdrawing group having a high acidity as one substituent of the ester group, i.e., an ester group having high reactivity and is commonly used in a variety of chemical syntheses, for example, in the field of polymer chemistry and peptide synthesis. Practically, for example, phenol esters, thiophenol esters, N-hydroxyamine esters, and esters of heterocyclic hydroxy compounds are known as active ester groups having much higher activity than, for example, alkyl esters.

Examples of such active ester groups include a p-nitrophenyl active ester group, an N-hydroxysuccinimide active ester group, a succinimide active ester group, a phthalic imide active ester group, and a 5-norbornene-2,3-dicarboximide active ester group, and preferred are a p-nitrophenyl active ester group and an N-hydroxysuccinimide active ester group, and most preferred is a p-nitrophenyl active ester group.

The proportion of the structural unit derived from a monomer represented by General Formula [2] in the polymer is usually 1 to 50 mol %, preferably 1 to 30 mol %, and most preferably 1 to 20 mol % with respect to the total structural units of the polymer. The monomers represented by General Formula [2] may be used alone or in combination of two or more thereof.

In General Formula [3], $R_4$ is a hydrogen atom or a methyl group, and Z is an alkyl group having 1 to 20 carbon atoms. At least one of $A_1$, $A_2$, and $A_3$ is a hydrolyzable alkoxy group, and the others are alkyl groups. A functional group producing a silanol group by hydrolysis is a group being readily hydrolyzed by contact with water to generate a silanol group, and examples thereof can include a halogenated silyl group, an alkoxysilyl group, a phenoxysilyl group, and an acetoxysilyl group. Among these groups, an alkoxysilyl group, a phenoxysilyl group, and an acetoxysilyl group are preferred because of not containing halogens, and, in particular, an alkoxysilyl group is most preferred in terms of easily producing a silanol group.

Examples of the monomer represented by General Formula [3] can include (meth)acryloxyalkylsilane compounds, such as 3-(meth)acryloxypropenyltrimethoxysilane, 3-(meth)acryloxypropylbis(trimethylsiloxy)methylsilane, 3-(meth)acryloxypropyldimethylmethoxysilane, 3-(meth)acryloxypropyldimethylethoxysilane, 3-(meth)acryloxypropylmethyldimethoxysilane, 3-(meth)acryloxypropylmethyldiethoxysilane, 3-(meth)acryloxypropyltrimethoxysilane, 3-(meth)acryloxypropyltriethoxysilane, 3-(meth)acryloxypropyltris(methoxyethoxy)silane, 8-(meth)acryloxyoctanyltrimethoxysilane, and 11-(meth)acryloxyundenyltrimethoxysilane. Among these monomers, 3-methacryloxypropyltrimethoxysilane, 3-methacryloxypropyltriethoxysilane, 3-methacryloxypropyldimethylmethoxysilane, and 3-methacryloxypropyldimethylethoxysilane are preferred, for example, in terms of high copolymerizability with an ethylene-based unsaturated polymerizable monomer having an alkylene glycol residue and in terms of easy acquisition. These monomers may be used alone or in combination of two or more thereof.

The proportion of the structural unit derived from a monomer represented by General Formula [3] in the polymer is usually 1 to 20 mol %, preferably 2 to 15 mol %, and more preferably 2 to 10 mol % with respect to the total structural units of the polymer.

The polymer may include a structural unit other than the structural units derived from the monomers of General Formulae [1] to [3] mentioned above. For example, a structural unit derived from an ethylene-based unsaturated polymerizable monomer (d) including an alkyl group may be copolymerized. Examples of the monomer (d) preferably include n-butyl methacrylate, n-dodecyl methacrylate, and n-octyl methacrylate. When the polymer includes a structural unit derived from the monomer (d), the content thereof is usually 0 to 60 mol %, preferably 0 to 50 mol %, and more preferably 0 to 40 mol %.

The method for synthesizing the polymer is not particularly limited. For example, it is preferable to radically polymerize a mixture containing monomers having structures represented by General Formulae [1] to [3] described above in the presence of a polymerization initiator in a solvent.

The solvent may be any solvent that can dissolve the respective ethylene-based unsaturated polymerizable monomers, and examples thereof can include methanol, ethanol, t-butyl alcohol, benzene, toluene, tetrahydrofuran, dioxane, dichloromethane, and chloroform. These solvents may be used alone or in combination of two or more thereof. When the high-molecular compound is applied to a plastic base material, ethanol and methanol are preferred because they do not denature the base material.

The polymerization initiator may be any ordinary radical initiator, and examples thereof can include azo compounds, such as 2,2'-azobisisobutyronitrile (hereinafter referred to as "AIBN") and 1,1'-azobis(cyclohexane-1-carbonitrile); and organic peroxides, such as benzoyl peroxide and lauryl peroxide.

The chemical structure of the polymer may be in any form, such as random, block, and graft, as long as the chemical structure of the polymer includes structural units derived from monomers represented by General Formulae [1] to [3] mentioned above. The number-average molecular weight of the polymer of the present embodiment is preferably greater than or equal to 5000 and more preferably greater than or equal to 10000, because of the ease of separation of the polymer from unreacted monomers and purification thereof.

It is possible to easily impart a property of suppressing nonspecific adsorption of physiologically active substances and a property of immobilizing a specific physiologically active substance by coating the inner surface 61a and the upper surface 60b with the polymer. Furthermore, since the polymer has a crosslinked structure (i.e., polymer chains are crosslinked to one another) and is therefore insoluble, it is possible to reduce the signal lowering due to washing and sterilization treatment of the cell accommodating chip 60.

The coating of the inner surface 61a and the upper surface 60b with the polymer is performed by, for example, (i) preparing a solution by dissolving the polymer in an organic solvent at a concentration of 0.05 to 10 wt %, (ii) applying the solution to the inner surface 61a and the upper surface 60b by a known method such as dipping or spraying, and (iii) drying the applied solution at room temperature or with heating. In the (i) preparation of the solution, the solution may contain a component other than the polymer and the organic solvent. For example, the solution may contain, for example, a surfactant for uniform application and an adhesion auxiliary for further enhancing the adhesion.

Subsequently, the polymer molecules are crosslinked by an appropriate method. In particular, in the present embodiment, since the polymer has a functional group producing a silanol group by hydrolysis, one method is to use a solution mixture containing water in an organic solvent. That is, the functional group producing a silanol group by hydrolysis is hydrolyzed by the contained water to generate silanol groups in the polymer. Subsequently, silanol groups or a silanol group and another functional group undergo dehydration by, for example, heating, and the polymer molecules bind to each other. Consequently, the polymer becomes insoluble. Considering the ease of preparation of the solution, it is preferable that the water content is about 0.01 to 15 wt %.

As the organic solvent, a single solvent, such as ethanol, methanol, t-butyl alcohol, benzene, toluene, tetrahydrofuran, dioxane, dichloromethane, chloroform, acetone, or methyl ethyl ketone, or a solvent mixture thereof is used. In particular, ethanol and methanol are preferred because they do not denature the cell accommodating chip 60 and are readily dried. In addition, ethanol and methanol are preferred because they can mix with water at arbitrary ratios even in the case of hydrolyzing the polymer.

In the step of drying the solution dissolving the polymer of the present embodiment after application onto the inner surface 61a and the upper surface 60b, the silanol group of a polymer molecule forms crosslinking with a silanol group, a hydroxyl group, an amino group, or the like of another polymer molecule through dehydration condensation. Furthermore, even when the inner surface 61a and/or the upper surface 60b has, for example, a hydroxyl group, a carbonyl group, or an amino group, similarly, the polymer can chemically bind to the base material surface through dehydration condensation. Since the covalent bond formed by dehydration condensation of a silanol group has a property of being hardly hydrolyzed, the polymer (coating layer 62) coating the base material surface is not easily dissolved and not easily peeled off. The dehydration condensation of a silanol group is accelerated by heat treatment. It is preferable to perform the heat treatment within a temperature range where the polymer is not denatured by the heat, for example, at 60° C. to 120° C. for 5 minutes to 24 hours.

As the material of the cell accommodating chip 60 according to the present embodiment, although glass, plastic, metals, and other materials can be used, plastic is preferred and a thermoplastic resin is more preferred in terms of the ease of surface treatment and mass productivity.

The thermoplastic resin is not particularly limited, but is preferably a linear polyolefin, such as polyethylene or polypropylene; polystyrene; a cyclic polyolefin; or a fluorine-containing resin to ensure transparency.

In order to enhance the adhesion between the coated polymer (coating layer 62) and the inner surface 61a and the upper surface 60b, it is preferable to active the inner surface 61a and/or the upper surface 60b. The method for activation is preferably a plasma treatment under conditions, such as an oxygen atmosphere, an argon atmosphere, a nitrogen atmosphere, or an air atmosphere; or a treatment with an excimer laser, such as ArF or KrF excimer laser. Among these methods, a plasma treatment in an oxygen atmosphere is preferable.

By applying the polymer to the inner surface 61a and/or the upper surface 60b, it is possible to easily produce a biochip substrate where the nonspecific adsorption of physiologically active substances is suppressed. In addition, the polymer has a crosslinked structure and thereby can make the coating layer 62 insoluble.

By using the cell accommodating chip according to the present embodiment, it is possible to immobilize various physiologically active substances. Examples of the physiologically active substance to be immobilized include nucleic acids, aptamers, proteins, oligopeptides, sugar chains, and glycoproteins. For example, in the case of immobilizing a nucleic acid, it is preferable to introduce an amino group for enhancing the reactivity with an active ester group. Although the introduction position of the amino group may be a polymer chain end or a side chain (also referred to as "branch"), it is preferable that the amino group is introduced into the end of the molecular chain.

In the immobilization of a physiologically active substance on the biochip substrate in the present embodiment, a method by spot application of a liquid in which the physiologically active substance is dissolved or dispersed is preferable.

After the spot application, the physiologically active substance is immobilized on the surface by being left to stand. For example, in the case of using an aminated nucleic acid, the aminated nucleic acid can be immobilized by being left to stand at from room temperature to 80° C. for 1 hour. A higher treatment temperature is preferable. It is preferable that the liquid for dissolving or dispersing the physiologically active substance is alkaline.

After washing, the functional group on the substrate surface other than the portion on which the physiologically active substance is immobilized is inactivated. In the case of an active ester or an aldehyde group, it is preferable that the inactivation is performed with an alkali compound or a compound having a primary amino group.

As the alkali compound, for example, sodium hydroxide, potassium hydroxide, sodium carbonate, sodium hydrogen carbonate, disodium hydrogen phosphate, calcium hydroxide, magnesium hydroxide, sodium borate, lithium hydroxide, and potassium phosphate can be preferably used.

As the compound having a primary amino group, for example, methylamine, ethylamine, butylamine, glycine, 9-aminoaquazine, aminobutanol, 4-aminobutyric acid, aminocaprylic acid, aminoethanol, 5-amino-2,3-dihydro-1,4-pentanol, aminoethanethiol hydrochloride, aminoethanethiol sulfate, 2-(2-aminoethylamino)ethanol, 2-aminoethyl dihydrogen phosphate, aminoethyl hydrogen sulfate, 4-(2-aminoethyl)morpholine, 5-aminofluorescein, 6-aminohexanoic acid, aminohexyl cellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenylacetic acid, and aminonaphthalene can be preferably used, and aminoethanol and glycine are most preferable.

Method of Using Cell Accommodating Chip

Figure 7:
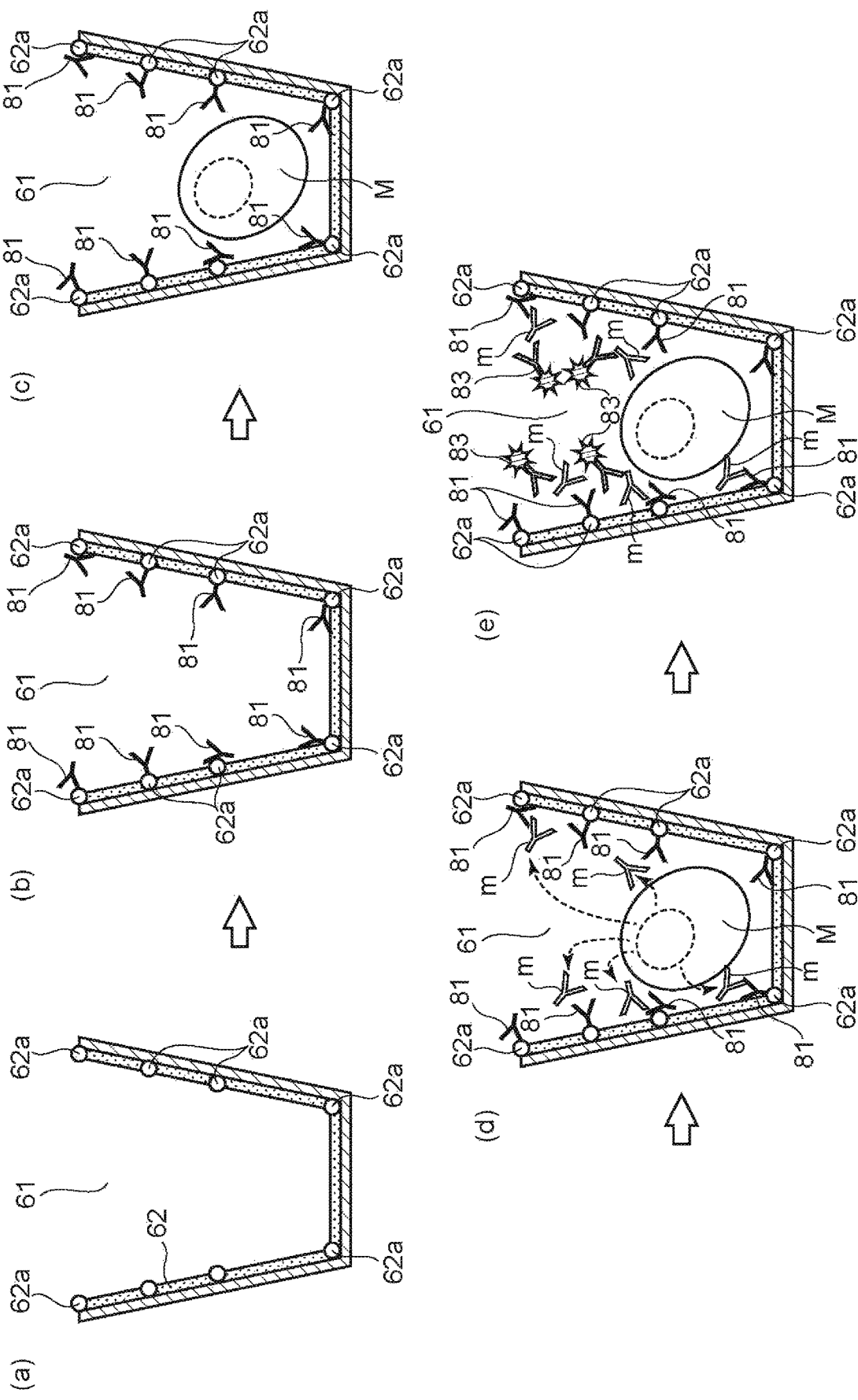
FIG. 7 is a diagram including schematic views (a) to (e) for explaining a method for using the cell accommodating chip shown in FIG. 6.

FIG. 7 is a diagram including schematic views (a) to (e) for explaining a method for using the cell accommodating chip 60 structured as described above.

First of all, in the coating layer 62 formed on the inner surface 61a of a well 61 (FIG. 7(a)); a predetermined functional group 62a, for example, an active ester group, of a functional group-containing material contained in the coating layer is bound to a specific binding material 81, such as a primary antibody (FIG. 7(b)). Here, a coupling solution containing the specific binding material 81 that binds the predetermined functional group 62a and a produced substance m that is produced by a cell M to be accommodated in the well 61 is used, and the coupling solution is introduced on the cell accommodating chip 60. Consequently, the predetermined functional group 62a and the specific binding material 81 are bound to each other.

In the case where an active ester or its derivative is used as the predetermined functional group 62a, the coupling solution is preferably alkaline and, specifically, preferably has a pH of 7 to 10. By using such a coupling solution, a natural state due to buffer action can be maintained, the specific binding material 81 (e.g., a protein) is prevented from being damaged by denaturation or the like, and good binding between the predetermined functional group 62a and the produced substance m can be obtained.

In addition, the specific binding material 81 is a binding substance that specifically binds to the produced substance. The specific binding material 81 is not limited to a primary antibody and may be an antigen or a substance other than protein. The specific binding material 81 used in the present disclosure is, for example, a chemical material such as a protein including cytokine, an immunoglobulin, an anti-immunoglobulin, and a hormone.

After washing the inside of the well 61, an incubation medium containing a cell M is accommodated in the well 61, and the cell M is incubated in the well 61. (FIG. 7(c)). The cell M generates a produced substance m, such as a produced antibody, by the incubation, and the produced substance m binds to the specific binding material 81 in the well 61 (FIG. 7(d)). As a result, the predetermined functional group 62a binds to the produced substance m via the specific binding material 81. The present disclosure can be applied to the identification of all cell types. The cell types are, for example, immune cell lines, such as B cells, T cells, and dendritic cells; cancer cell lines, such as CTC cells; stem cell lines, such as iPS cells and ES cells; hybridomas; CHO cells; and yeast cells. The produced substance is a protein including a cytokine, an immunoglobulin, an anti-immunoglobulin, and a hormone, or a chemical material, such as a vitamin.

After washing the inside of the well 61, an optical information-holding substance 83, such as a fluorescent molecule (e.g., fluorescence-attached secondary antibody), specifically binding to the produced substance m or the specific binding material 81 is bound thereto (FIG. 7(e)). Thus, the produced substance m produced by the cell M is bound to the specific binding material 81 bound onto the coating layer 62 in the well 61 accommodating the cell M; the optical information-holding substance 83 is bound to the produced substance m or the specific binding material 81; and the optical information of the optical information-holding substance 83 is detected. Consequently, it is possible to precisely identify a target sample using the well 61 as a marker, while maintaining the cell M and the produced substance m in the well 61 in a wet state.

Screening Method

The screening apparatus 1 structured as described above collects a target sample using the above-described cell accommodating chip 60 as follows.

Figure 8:
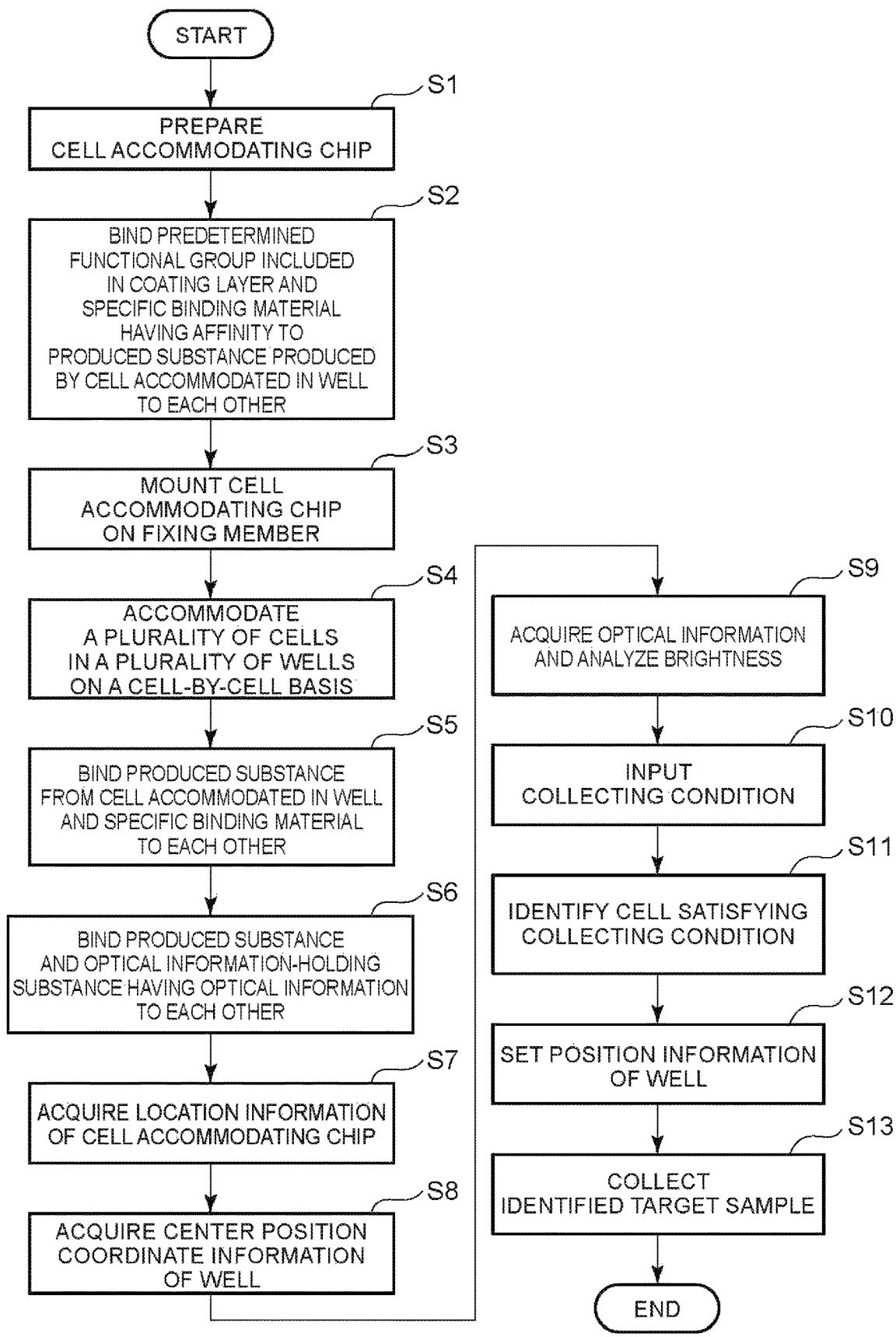
FIG. 8 is a flow chart illustrating a screening method using the cell accommodating chip shown in FIG. 7.

FIG. 8 is a flow chart illustrating a screening method using the cell accommodating chip 60 shown in FIG. 7, and FIG. 9 are schematic views for explaining each step of FIG. 8.

Figure 9A:
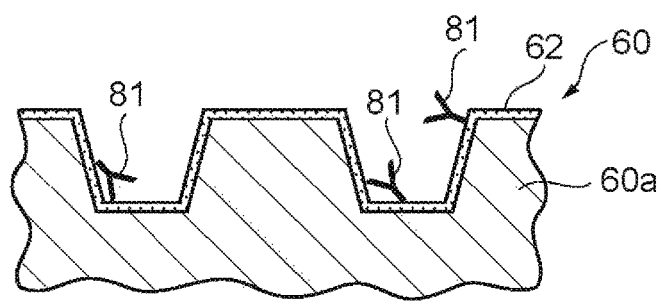
FIGS. 9A to 9D are schematic views for explaining each step of FIG. 8.

As shown in FIG. 8, a cell accommodating chip 60 configured as described above is prepared (Step S1), and a predetermined functional group 62a (see FIG. 7) contained in a coating layer 62 and a specific binding material 81 having affinity to a produced substance m produced by the cell accommodated in a well 61 are bound to each other (Step S2) (FIG. 9A). For example, a coupling solution containing a primary antibody is added dropwise or applied onto the coating layer 62 in the wells 61 to bind the primary antibody thereto.

Subsequently, the top of the cell accommodating chip 60 and the insides of the wells 61 are washed to remove the specific binding material not bound to the coating layer 62. After the washing, the cell accommodating chip 60 is mounted on the securing member 120 of the screening apparatus 1 (Step S3). Step S3 may be performed between Step S1 and Step S2.

Figure 9B:
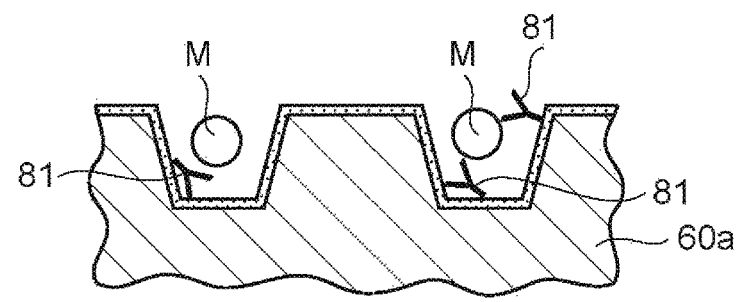

Subsequently, a liquid (e.g., incubation medium) containing a plurality of cells M is introduced to the wells 61 on the cell accommodating chip 60 to accommodate the plurality of cells M in the plurality of wells 61 on a cell-by-cell basis (Step S4) (FIG. 9B). The introduced liquid is left to stand for a predetermined period of time for waiting that each cell precipitates and enters into each well one by one. The cells M not accommodated in the wells 61 are removed by washing.

Figure 9C:
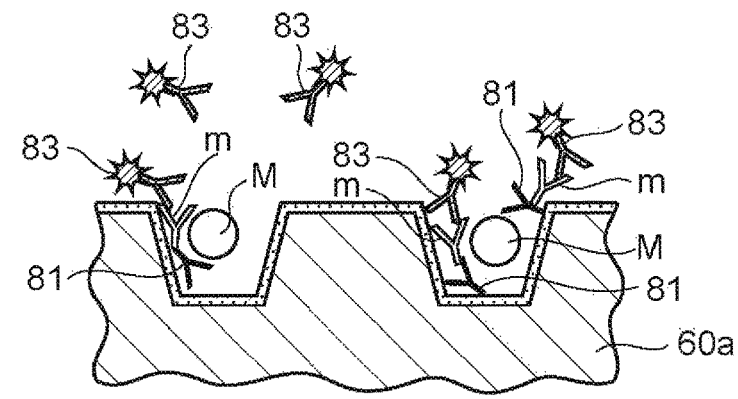

After the washing, the cell M accommodated in the well 61 is incubated to stimulate the production of a produced substance m, and the produced substance m produced by the cell M and the specific binding material 81 are bound to each other (Step S5). The cell incubation conditions (e.g., temperature, type of gas, and concentration) can be selected depending on the cell type, a purpose, etc. The incubation time of the cell M accommodated in the well 61 can be changed as needed. Subsequently, the produced substance m and the optical information-holding substance 83 having optical information, such as a fluorescent molecule, specifically binding to the produced substance m are bound to each other (Step S6) (FIG. 9C). For example, a solution containing a fluorescence-attached secondary antibody is added dropwise onto the cell accommodating chip 60, and this fluorescence-attached secondary antibody is bound to the produced substance m. The optical information-holding substance 83 may be a functional group-attached fluorescent dye, a biotinated antibody+avidinated fluorescent dye, a fluorescent bead-attached secondary antibody, or the like, in addition to the fluorescence-attached secondary antibody. The treatment of Step S6 may be performed simultaneously with the treatment of Step S5. Subsequently, the top of the cell accommodating chip 60 and the insides of the wells 61 are washed, and the optical information-holding substance 83 not bound to the produced substance m or the specific binding material 81 is removed.

Subsequently, for example, information on a reference position of the cell accommodating chip or a correction parameter is acquired as location information of the cell accommodating chip 60 (Step S7), and the center position coordinate information of each well is acquired by image analysis (Step S8).

Subsequently, the cell accommodating chip 60 is irradiated with light, and the optical information of the optical information-holding substance 83 is acquired and is subjected to brightness analysis (Step S9). The optical information of the optical information-holding substance 83 fluorescent based on the photoirradiation in Step S9 may be acquired, or the optical information of the previously fluorescent optical information-holding substance 83 may be acquired. As the brightness analysis, a change with time of the fluorescent information obtained from the optical information-holding substance 83 may be measured.

Subsequently, based on the acquired brightness information, a collecting condition of microparticles desired by a user may be, for example, the brightness of a fluorescence is higher than a predetermined threshold value, or the brightness of at least one of the fluorescences is higher than a predetermined threshold value in the case a plurality of fluorescences (e.g., different fluorescent colors) are used, or any combination thereof. In addition, the brightness of any fluorescence may be combined with those excluded from the collection (those lower than a threshold value). Some conditions determined as described above are input (Step S10), and the cell M is identified as a target sample based on the collecting condition (Step S11). For example, the cell M accommodated in the well 61 emitting light with brightness satisfying the above-mentioned collecting condition is identified as a target sample.

Figure 9D:
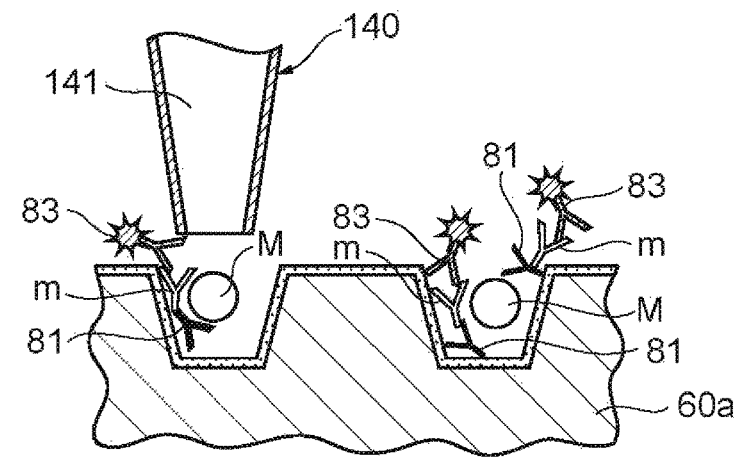

Subsequently, the center position of the suction/discharge capillary 140 is acquired by, for example, image analysis, and the center position or a position shifted from the center position by a predetermined distance is set as the center position (position information) of each well in the cell collection (Step S12). The center position of the well 61 accommodating the target sample is moved so as to fit the center position of the well set in Step S12, and target samples identified in Step S11 are sequentially collected (Step S13) (FIG. 9D). The collected target samples are accommodated in predetermined wells 51 on the accommodating plate 50 set by the user in advance.

Evaluation of Hydrophilicity of Cell Accommodating Chip

Figure 10:
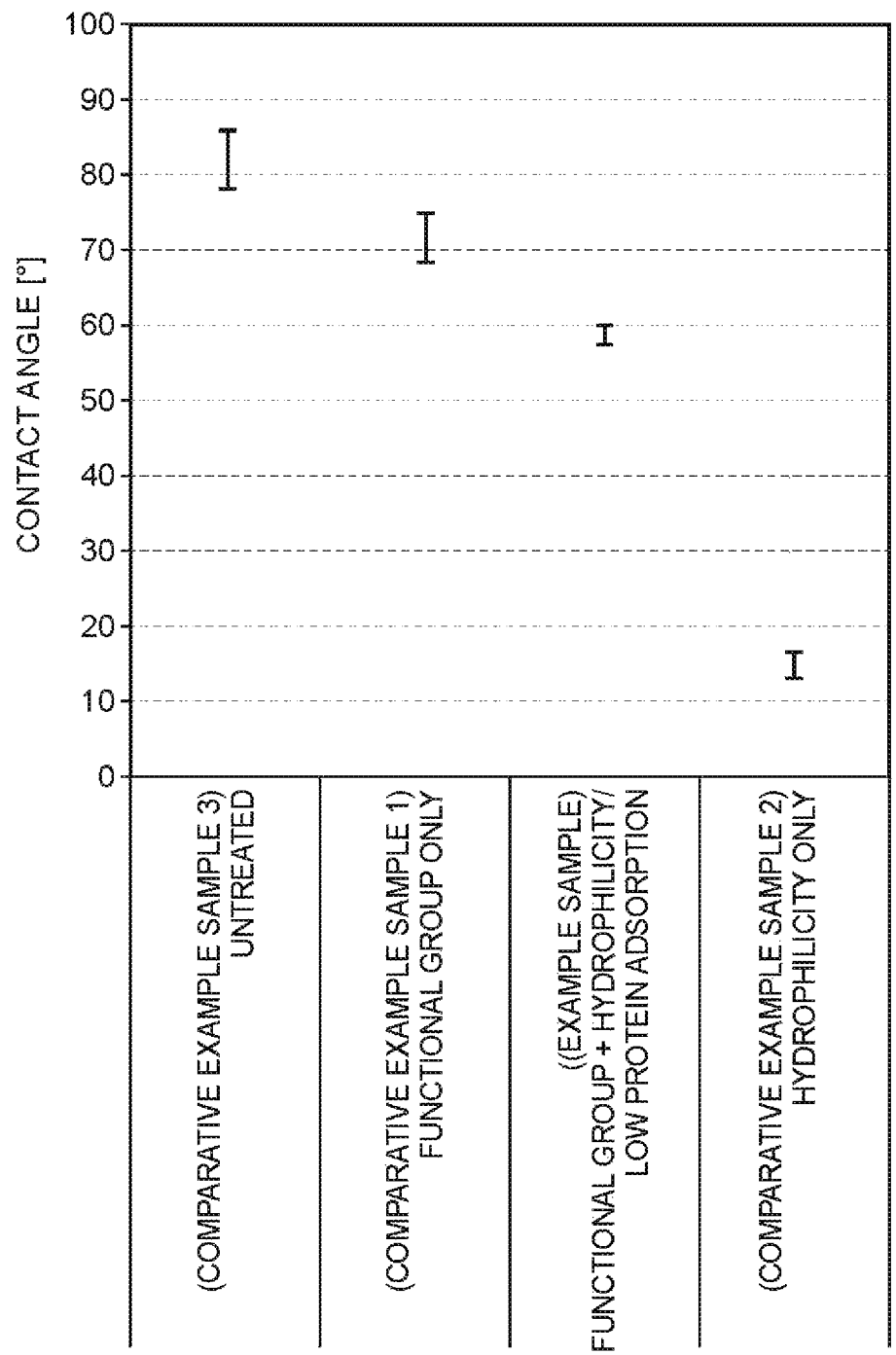
FIG. 10 is a graph showing the results in measurement and comparison of contact angles between a variety of cell accommodating chips and distilled water.

FIG. 10 is a graph showing the results of measurement and comparison of contact angles between a variety of cell accommodating chips and distilled water.

In the present evaluation, as an Example Sample 1, a coating layer containing a first material having both hydrophilicity and low protein adsorption, a second material which is a functional group-containing material, and a third material which is a crosslinking component (see FIG. 7(a)) was used. As a Comparative Example Sample 1, a coating layer containing only a functional group-containing material was used; as a Comparative Example Sample 2, a coating layer containing only a hydrophilic material was used; and as a Comparative Example Sample 3, an untreated cell accommodating chip that does not have a coating layer was used. In all samples, the material and shape of the substrates and the method for producing the substrates were the same. The Example Sample will now be specifically described.

Synthesis Example of High-Molecular Compound Used in Example Sample

Polyethylene glycol methyl ether methacrylate (PEGMA, number-average molecular weight Mn: 468, manufactured by Shin-Nakamura Chemical Co., Ltd.) as the first material, p-nitrophenyloxycarbonyl-polyethylene glycol methacrylate (MEONP, manufactured by Nard Institute, Ltd.) as the second material, and 3-methacryloxypropyldimethyl-methoxysilane (MPDMS, manufactured by GELEST, INC.) as the third material were dissolved in dehydrated ethanol in order at concentrations of 0.90 mol/L, 0.05 mol/L, and 0.05 mol/L, respectively, to produce a monomer mixture solution. Furthermore, 2,2-azobisisobutyronitrile (AIBN, manufactured by FUJIFILM Wako Pure Chemical Corporation) was added thereto at a concentration of 0.002 mol/L, and the monomer mixture solution was stirred until uniform. Subsequently, the solution was reacted in an argon atmosphere at 60° C. for 4 hours, and the reaction solution was then added dropwise to diethyl ether to collect the precipitate. The resulting high-molecular compound Was measured by $^1$H-NMR in heavy ethanol solvent, and the composition of the high-molecular compound was calculated from the integrated values of each of a peak attributable to methylene binding to Si of MPDMS appearing at about 0.7 ppm, a peak attributable to the terminal methoxy group of PEGMA appearing at about 3.4 ppm, and peaks attributable to the benzene ring of MEONP appearing at about 7.4 ppm and about 8.3 ppm. Table 1 shows the results.

TABLE 1

| Composition (mol %) of high-molecular compound | | |
|---|---|---|
| PEGMA | MEONP | MPDMS |
| 91 | 5 | 4 |

Method for Producing Example Sample

To a substrate, the surface of a substrate was subjected to oxidation treatment by plasma treatment in an oxygen atmosphere. The substrate was immersed in a 0.3 wt % ethanol solution of the high-molecular compound obtained in the synthesis example of a high-molecular compound and was then heat-dried at 60° C. for 18 hours to introduce, on the substrate surface, a layer containing a high-molecular compound consisting of an ethylene-based unsaturated polymerizable monomer having an alkylene glycol residue, an ethylene-based unsaturated polymerizable monomer having an active ester group, and an ethylene-based unsaturated polymerizable monomer having a crosslinkable functional group.

The contact angle was measured in accordance with JIS R3257 and the contact angle was calculated by a static method as shown below. The contact angle θ (°) was determined from the radius r (mm) and the height h (mm) when 1 μL of distilled water was dropped onto a cell accommodating chip. Here, the radius r is a radius of the surface of the water drop in contact with the chip surface, and the height h is a height from the chip surface to the top of the water drop. The average value when 6 points were measured per sample was calculated.

As shown in FIG. 10, when the coating layer contains a functional group-containing material only (Comparative Example Sample 1), the contact angle between the coating layer and distilled water is 69° to 75°, and an average value is 72°. In contrast, the coating layer of the present disclosure (Example Sample 1) contains a material having both hydrophilicity and low protein adsorption and a functional group-containing material, and the contact angle is 57° to 59°, an average value is 59°, and it is demonstrated that the hydrophilicity has been considerably improved. When the coating layer contains a hydrophilic material only (Comparative Example Sample 2), the contact angle between the cell accommodating chip and a liquid containing cells is 14° to 17°, an average value is 15°, it is difficult to bind a specific binding material having affinity to a produced substance, and the cell accommodated in the well and proteins such as the produced substance could adsorb to the coating layer. In the case of an untreated cell accommodating chip (Comparative Example Sample 3), the contact angle is 78° to 86°, an average value is 83°, and the wettability is obviously low. These measurement results demonstrate that the coating layer of the present embodiment is capable of suppressing adsorption of proteins and achieving satisfactory hydrophilicity while allowing the binding of the specific binding material having affinity to the produced substance.

Evaluation of Hydrophilicity Based on Bubble Ratio of Well

Since the wells formed in the cell accommodating chip are minute, the hydrophilicity of the cell accommodating chip containing the wells highly affects the inflow of a liquid containing cells into the wells. Accordingly, in order to verify and evaluate the influence of the contact angle of the cell accommodating chip on the bubble ratio occurring in the wells, which is an index of hydrophilicity, the following test was performed.

First of all, each of the cell accommodating chips was set in a securing member, PBS (phosphate buffered saline) of ordinary temperature was introduced on the cell accommodating chip, and the proportion of the number of wells having bubbles therein in random 500 wells on the chip was determined as a bubble ratio. The bubble ratios were determined immediately after introduction of the buffer (bubble ratio (1)), after an elapse of time t (t=5 minutes) after introduction of the buffer (bubble ratio (2)), and after an elapse of time 2t (10 minutes) after introduction of the buffer (bubble ratio (3)). In the present evaluation, the same Example Sample and Comparative Example Samples as those in the evaluation of hydrophilicity were used. The results are shown in Table 2.

TABLE 2

| | Contact angle (average value) | Bubble ratio (1) | Bubble ratio (2) | Bubble ratio (3) |
|---|---|---|---|---|
| Example Sample-1 | 59° | 100% | 0% | 0% |
| Comparative Example Sample 1 | 72° | 100% | 100% | 96% |
| Comparative Example Sample 2 | 15° | 0% | 0% | 0% |
| Comparative Example Sample 3 | 83° | 100% | 100% | 100% |

It is demonstrated froth the results of Table 2 that in the case of the coating layer of the present embodiment (Example Sample 1), the bubble ratios (1) to (3) of the wells were 100%, 0%, and 0%, respectively, although bubbles were found in a large number of wells immediately after introduction of PBS, the bubbles promptly escaped, and the bubbles escaped from almost all wells after an elapse of a certain time. In contrast, in the case of the coating layer containing the functional group-containing material only (Comparative Example Sample 1), the bubble ratios (1) to (3) of the wells were 100%, 100%, and 96%, respectively, bubbles were formed in almost all wells immediately after introduction of PBS, and the bubbles remained in almost all wells even after an elapse of a predetermined time. In addition, in the case of a coating layer containing a hydrophilic material only (Comparative Example Sample 2), the bubble ratios (1) to (3) of the wells were all 0%, wells having bubbles were not found immediately after introduction of PBS and also after an elapse of a predetermined time. In the case of the untreated cell accommodating chip (Comparative Example Sample 3), the bubble ratios (1) to (3) of the wells were all 100%, bubbles were formed in all wells immediately after introduction of PBS, and the bubbles remained in all wells even after an elapse of a predetermined time.

When accommodating cells in the wells, a liquid containing the cells (also referred to as cell suspension) is introduced on the cell accommodating chip and is left to stand, and the cells then slowly precipitate in the liquid and are accommodated in the wells. However, if the wettability of the surface of the cell accommodating chip and the surface of the well is low, bubbles are produced in the well, the progress of precipitation of the cell is prevented by the bubbles in the well, and it is impossible to accommodate the cell in the well. Accordingly, the surface of the cell accommodating chip needs to have hydrophilicity that allows bubbles in the well to escape before the cell precipitates in the liquid. According to the present embodiment, it was confirmed that if the contact angle of the surface of the cell accommodating chip is less than or equal to 60°, the surface of the cell accommodating chip has the sufficient hydrophilicity for preventing bubbles from being produced in the well, and a cell can be positively accommodated in a fine well.

Evaluation of Low Cell Adhesion Property of Cell Accommodating Chip

Subsequently, the adhesion rates of cells to the coating layers similar to the samples used in the evaluation shown in FIG. 10 were measured and compared.

The measurement and evaluation of the adhesion rates of cells were performed as follows. As shown in FIG. 8, firstly, a primary antibody-containing coupling solution was added dropwise onto each of the cell accommodating chips to bind the primary antibody. Subsequently, the surface of the cell accommodating chip was washed to remove the unbound primary antibody and the components of the coupling solution. After the washing, each of the cell accommodating chips was set to the securing member, an incubation medium containing a plurality of 293T cells was introduced on the cell accommodating chip, and the plurality of cells were accommodated in a plurality of wells on a cell basis. Subsequently, the cells not accommodated in the wells were removed by washing. After the washing, the cell accommodating chip and the cells accommodated in the wells are incubated for 60 minutes, and when the 48 cells stored in the wells on the cell accommodating chip were tried to be collected with a cell-screening apparatus including a collection mechanism, the proportion of the cells that adhered to the surface of the cell accommodating chip and could not be collected was defined as the adhesion rate. The measurement points were n=48.

In the present evaluation, the same Example Sample 1 and Comparative Example Samples 1 and 2 as those in the aforementioned evaluation of hydrophilicity were used. The results are shown in Table 3.

TABLE 3

|  | Cell type | Contact angle (average value) | Adhesion rate |
| --- | --- | --- | --- |
| Example Sample 1 | 293T | 59° | 8% |
| Comparative Example Sample 1 | 293T | 72° | 96% |
| Comparative Example Sample 2 | 293T | 15° | 83% |

As shown in Table 3, it is demonstrated that in the case of the coating layer of the present embodiment (Example Sample 1), the adhesion rate of 293T cells was about 8% (4 cells), and, most of the 293T cells did not adhere to the coating layer. In contrast, it is demonstrated that in the case of the coating layer containing the functional group-containing material only (Comparative Example Sample 1), the adhesion rate of the 293T-cells was about 96% (46 cells), and most of the cells adhered to the coating layer. It is also demonstrated that in the case of the coating layer containing the hydrophilic material only (Comparative Example Sample 2), the adhesion rate was about 83% (40 cells), and most of the cells adhered to the coating layer. The results demonstrated that according to the coating layer of the present embodiment, the adhesion rate of cells to the coating layer is remarkably low, the coating layer in a well hardly adheres to the cell accommodated in the well, and a favorable low cell adhesion property can be achieved.

Evaluation of Affinity to Specific Binding Material

In order to evaluate affinity of the active ester group to the specific binding material having affinity to the produced substance produced by a cell, interaction analysis between biotin immobilized to the substrate surface and avidin was performed. As an Example Sample 2, a cyclic polyolefin substrate having a coating layer made of the high molecule synthesized in the "(Synthesis example of high-molecular compound used in Example Sample)" described above was produced. As a Comparative Example Sample 4, a cyclic polyolefin substrate that does not have the coating layer was used.

Immobilization of Biotin and Interaction with Avidin

A biotin hydrazide solution adjusted to 1 mM with a carbonate buffer with a pH of 9.0 was spot-applied to the Example Sample 2 and the Comparative Example Sample 4 and was left to stand at 37° C. for 1 hour to immobilize biotin molecules to the substrate surface. After washing the substrate with pure water, the substrate was immersed in a Cy3-labeled Streptavidin solution adjusted to 2 μg/mL with PBS containing 0.1% Tween 20 for a reaction at room temperature for 1 hour to bind between biotin and avidin.

Interaction Analysis Between Biotin and Avidin

After washing of the substrate with PBS containing 0.1% Tween 20, the fluorescent signal (5) of the Cy3 dye at the portion to which the biotin hydrazide solution was spot-applied and the fluorescent signal (N) of the Cy3 dye at the portion to which the biotin hydrazide solution was not spot-applied were detected with a commercially available microarray scanner, and the results are shown in Table 4 as S/N ratios. By comparison of the S/N ratios of Example Sample 2 and Comparative Example Sample 4, it was shown that a biotin molecule having affinity to an avidin molecule used to resemble the produced substance produced by the cell can be simply immobilized to the substrate surface by using the Example Sample 2 having the active ester group.

TABLE 4

|  | Example Sample 2 | Comparative Example Sample 4 |
|---|---|---|
| S/N ratio | 378.2 | 5.2 |

Verification of Effect by Crosslinking

Subsequently, in order to show that the crosslinking of a polymer has an effect of preventing a reduction in the signal due to washing, the change in the adsorbed amount of proteins between before and after the washing with ethanol was verified. As an Example Sample 3, a polystyrene substrate having a coating layer made of the high molecule synthesized in the "(Synthesis example of high-molecular compound used in Example Sample)" described above was produced. As Comparative Example 5, a polystyrene substrate having a coating layer made of only a first material having both hydrophilicity and low protein adsorption and a second material that is the functional group-containing material was produced. As a Comparative Example Sample 6, a polystyrene substrate that does not have a coating layer was used. As the polystyrene substrate, a 96-well plate was used.

Adsorption of Protein

Ethanol was dispensed in a part of the wells of each of Example Sample 3, Comparative Example Sample 5, and Comparative Example Sample 6, and the wells were left to stand for 30 minutes. Ethanol was then removed followed by air drying at room temperature. A peroxidase-labeled avidin solution adjusted to 0.5 µg/mL with PBS was dispensed in each sample, and the samples were left to stand at room temperature for 1 hour to adsorb avidin to the substrate surface. After washing of the substrate with PBS containing 0.1% Tween 20, each well was color-developed with a commercially available coloring agent for HRP (manufactured by Sumitomo Bakelite Co., Ltd.), and the absorbance at 450 nm was measured with a commercially available plate reader to measure the adsorbed amount of avidin.

Measurement of Change in Adsorbed Amount of Protein

Regarding Example Sample 3, Comparative Example Sample 5, and Comparative Example Sample 6, the absorbance values of wells washed with ethanol and wells not washed are shown in Table 5. The absorbance was determined as the difference between the absorbance at 450 nm and the absorbance at 670 nm as a reference. In Example Sample 3, there was no significant change in the absorbance value between before and after washing, but in Comparative Example Sample 5, an increase in the absorbance value was observed after washing. From this fact, it is demonstrated that the influence on the coating layer by washing with ethanol was avoided by the effect of the crosslinked structure of Example Sample 3. In addition, in Comparative Example Sample 6 that does not have the coating layer, regardless of before or after washing, a high absorbance value is observed and, in comparison with Example Sample 3, low adsorption due to the first material can be confirmed.

TABLE 5

|  | Example Sample 3 | Comparative Example Sample 5 | Comparative Example Sample 6 |
|---|---|---|---|
| Absorbance (without washing) | 0.19 | 0.37 | 1.98 |
| Absorbance (with washing) | 0.12 | 1.1 | 1.9 |

As described above, according to the present embodiment, the surface of the coating layer 62 in a plurality of wells 61 has a low cell adhesion property and has affinity to the specific binding material 81 having affinity to the produced substance m produced by the cell M accommodated in the well 61. The liquid containing cells M can easily enter fine wells 61 by means of the hydrophilic material of the coating layer 62, the accuracy of accommodating a single cell in each well can be enhanced, and the accuracy and efficiency of identifying and isolating a target sample can be improved. In addition, since chips of the related art have a structure in which a substance (e.g., Ig antibody) having affinity to the produced substance is bound on a chip in advance, it is difficult to store the chip for a long time, and accuracy may decrease due to drying or the like. In contrast, according to the present embodiment, the surface of the coating layer 62 has affinity to the specific binding material 81, and thereby there is no need to bind the specific binding material 81 having affinity to the produced substance m on the cell accommodating chip 60 in advance, and the reduction in accuracy due to drying or the like can be prevented. In addition, since the inside of the well 61 is hardly dried by the hydrophilicity of the coating layer 62 compared to the one of the related art, the inside of the well 61 can be kept wet even after binding of the specific binding material 81, and a reduction in accuracy due to drying or the like of the specific binding material 81 can be prevented. In addition, the specific binding material 81 binds to the predetermined functional group 62a by the affinity of the surface of the coating layer 62 to the specific binding material 81, and the produced substance m produced by the cell M in the well 61 of the coating layer 62 binds to the specific binding material 81. Accordingly, the well 61 itself can be used as a labeling site in identification of a target sample, and the target sample can be identified without damaging the cell M. Furthermore, since the surface of the coating layer 62 has a low cell adhesion property, the cell M in the well 61 can be prevented from adhering to the inner surface of the well and the upper surface 60b of the substrate 60a, the cell M as a target sample can be collected at high efficiency without requiring coating treatment using a blocking reagent or the like, and when collecting cells, the cell M can be collected without being damaged. In addition, since the coating layer 62 contains a low protein adsorption material, when the produced substance m is a protein, nonspecific adsorption of the produced substance m to the surface of the cell accommodating chip is prevented, and good detection sensitivity can be maintained without requiring coating treatment using a blocking reagent or the like.

In addition, according to the present embodiment, a cell accommodating chip 60 including a coating layer 62 having a surface that has a low cell adhesion property and affinity to a specific binding material 81 having affinity to a produced substance m produced by a cell M accommodated in a well 61 is prepared; and a specific binding material 81 is bound to the surface of the coating layer 62, a liquid containing a plurality of cells M is introduced to the cell accommodating chip 60 to accommodate the plurality of cells M in a plurality of wells 61 on a cell basis to bind the produced substance m from the cell M accommodated in the well 61 to the specific binding material 81, which allows the produced substance m or the specific binding material 81 to bind an optical information-holding substance 83 having optical information. It is therefore possible to identify and isolate the target sample with high accuracy and high efficiency. In addition, easy collection without damaging cells M in cell collection can be achieved by simple treatment.

A cell accommodating chip according to the present embodiment and a screening method using the cell accommodating chip have been described above. However, the present disclosure is not limited to the above-described embodiment and can be variously modified and altered based on the technical idea of the present disclosure.

For example, in FIGS. 8 and 9A to 9D, the cell M accommodated in a well 61 emitting light with brightness satisfying the collecting condition is identified as a target sample (Step S11). That is, in FIGS. 8 and 9A to 9D, an optical information-holding substance 83 that specifically binds to the produced substance m (white Y in FIGS. 9A to 9D) that is secreted from the cell M is used, and the produced substance m produced by the cell M binds to the well 61 in which the cell M is accommodated. Accordingly, as described above, the timing of binding the optical information-holding substance 83 to the specific binding material 81 (Step S6) can be after Step S5 or simultaneous with Step S5.

In contrast, a screening method for identifying, as a target sample, the cell M accommodated in a well 61 other than the wells emitting light with brightness not lower than the threshold used in the above-described collecting condition may be used. Hereinafter, description of the same parts as those in the flow chart shown in FIG. 8 will be omitted, and different parts will be described.

Figure 11:
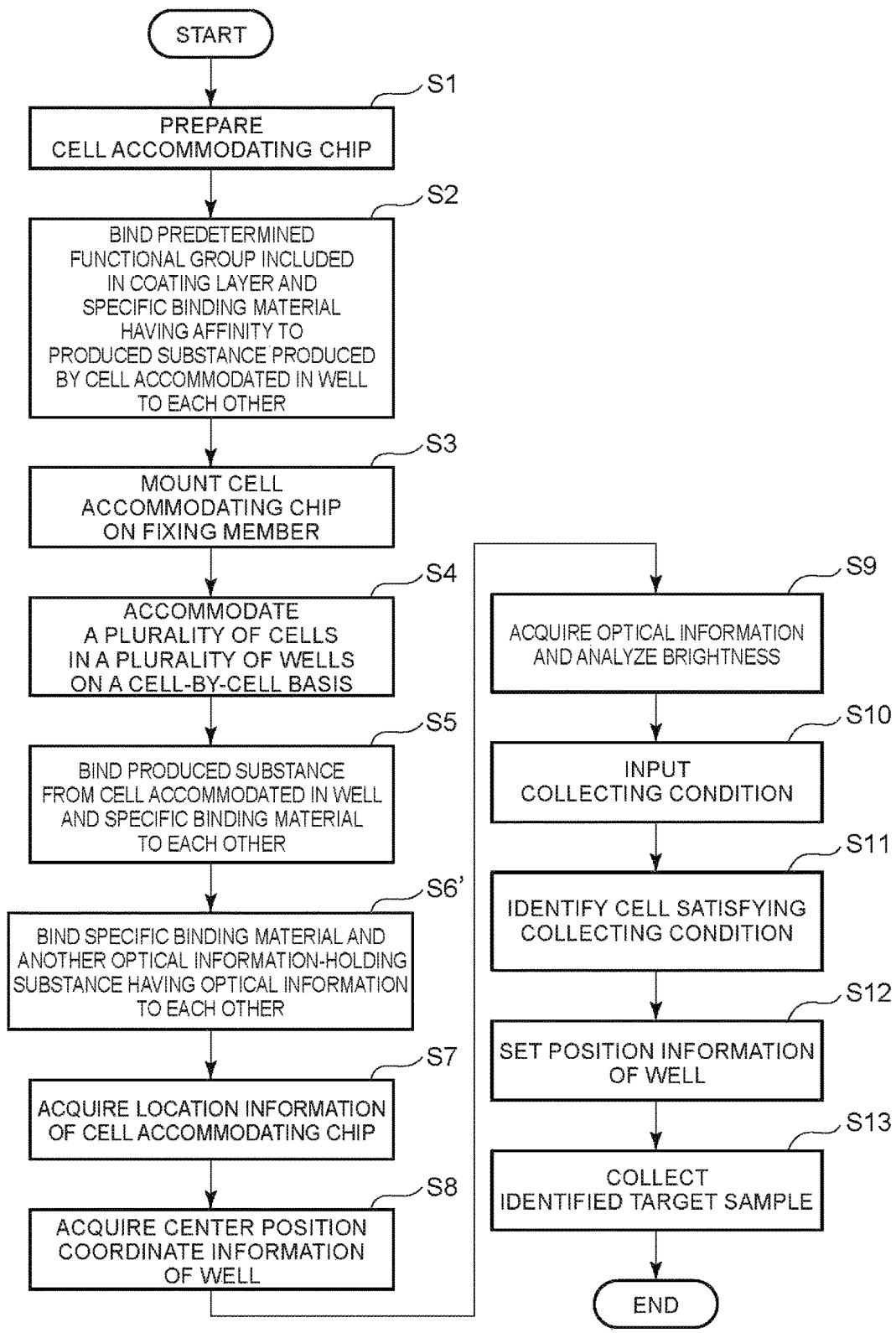
FIG. 11 is a flow chart illustrating a modified example of the screening method shown in FIG. 8.

As shown in FIG. 11, first of all, a plurality of cells M is accommodated in a plurality of wells 61 on a cell-by-cell basis (Step S4), and then each cell is incubated to stimulate the production of a produced substance m to bind the produced substance in produced by the cell M to the specific binding material 81 in the well 61 (Step S5). Consequently, the specific binding material 81 in the well 61 accommodating the cell M as a target sample is covered with the produced substance m, and the specific binding material 81 in the well 61 not accommodating the cell M as a target sample is not covered with the produced substance m. In this modification example, another optical information-holding substance not specifically binding to the produced substance m but specifically binding to the specific binding material 81 is used, and the another optical information-holding substance is bound to the specific binding material 81 (Step S6'). Consequently, the well 61 accommodating a cell M producing the produced substance m does not emit light, and the well 61 accommodating a cell M not producing the produced substance in emits light. Accordingly, in this method, Step S5 and Step S6' are not simultaneously performed, and Step S6' is performed after Step S5.

Subsequently, the optical information of the optical information-holding substance 83 is acquired and is subjected to brightness analysis (Step S9). Based on the acquired brightness information, a collecting condition of microparticles desired by a user is input (Step S10), and based on the collecting condition, a cell M is identified as a target sample (Step S11). The collecting condition is that light is not emitted or that the brightness is not higher than a predetermined threshold, and the cell M accommodated in a well 61 satisfying the collecting condition is identified as a target sample. By this method also, it is possible to collect a desired target sample.

What is claimed is:

1. A cell accommodating chip capable of accommodating a plurality of cells, the cell accommodating chip adapted for use in a screening apparatus for searching for a predetermined cell based on optical information emitted from a substance on the cell accommodating chip and selectively collecting the cell searched for, the cell accommodating chip comprising:
   a substrate composed of a light-transmitting material;
   a plurality of wells capable of accommodating cells, the plurality of wells being provided on at least one of main faces of the substrate; and
   a material of the cell accommodating chip is a thermoplastic resin,
   wherein each of the wells has a size accommodating to a size of the single cell of a target cell;
   the wells are recessed portions provided on an upper surface of the cell accommodating chip;
   a contact angle of the surface of the cell accommodating chip is 60° or less;
   a horizontal cross-sectional shape of the well is substantially circular; and
   a surface of the cell accommodating chip having the plurality of wells is coated with a polymer having a crosslinked structure, the polymer including a structural unit derived from a monomer is represented by the following General Formula [1], a structural unit derived from a monomer is represented by the following General Formula [2], and a structural unit derived from a monomer is represented by the following General Formula [3];

Formula [1]

General Formula [1]

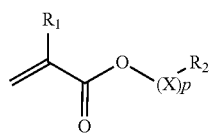

wherein $R_1$ represents a hydrogen atom or a methyl group; $R_2$ represents a hydrogen atom or an alkyl group having 1 to 20 carbon atoms; X represents an alkylene glycol residue having 1 to 10 carbon atoms; and p represents an integer of 1 to 100, and when p is an integer of greater than or equal to 2 but less than or equal to 100, any repeated X may be the same or may be different,

[Formula 2]

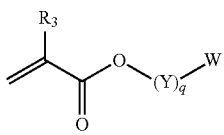

General Formula [2]

wherein $R_3$ represents a hydrogen atom or a methyl group; Y represents an alkyl group or an alkylene glycol residue having 1 to 10 carbon atoms; W represents an active ester group; and q represents an integer of 1 to 20, and when q is an integer of greater than or equal to 2 but less than or equal to 20, any repeated Y may be the same or may be different, Formula [3]

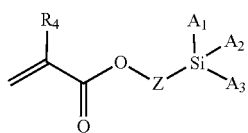

General Formula [3]

wherein $R_4$ represents a hydrogen atom or a methyl group; Z represents an alkyl group having 1 to 20 carbon atoms; and the rest of $A_1$, $A_2$, and $A_3$ is/are alkyl group(s).

2. The cell accommodating chip according to claim 1, wherein the structural unit derived from a monomer represented by General Formula [1] is methoxy polyethylene glycol acrylate or methoxy polyethylene glycol methacrylate.

3. The cell accommodating chip according to claim 2, wherein an average repeating number of ethylene glycol residues of the methoxy polyethylene glycol acrylate and/or the methoxy polyethylene glycol methacrylate is 3 to 100.

4. The cell accommodating chip according to claim 1, wherein the active ester group included in the structural unit derived from a monomer represented by General Formula [2] is one of a p-nitrophenyl active ester group and an N-hydroxysuccinimide active ester group.

5. The cell accommodating chip according to claim 1, wherein the thermoplastic resin is at least one selected from a group consisting of a linear polyolefin, polystyrene, a cyclic polyolefin and a fluorine-containing resin.

* * * * *